US012637520B2

(12) United States Patent
Rader et al.

(10) Patent No.: US 12,637,520 B2
(45) Date of Patent: May 26, 2026

(54) CONJUGATION CHEMISTRY FOR CATALYTIC ANTIBODY 38C2

(71) Applicant: UNIVERSITY OF FLORIDA RESEARCH FOUNDATION, INCORPORATED, Gainesville, FL (US)

(72) Inventors: Christoph Rader, Jupiter, FL (US); Dobeen Hwang, Palm Beach Gardens, FL (US)

(73) Assignee: University of Florida Research Foundation, Incorporated, Gainesville, FL (US)

( * ) Notice: Subject to any disclaimer, the term of this patent is extended or adjusted under 35 U.S.C. 154(b) by 985 days.

(21) Appl. No.: 17/770,922

(22) PCT Filed: Oct. 15, 2020

(86) PCT No.: PCT/US2020/055768
§ 371 (c)(1),
(2) Date: Apr. 21, 2022

(87) PCT Pub. No.: WO2021/080846
PCT Pub. Date: Apr. 29, 2021

(65) Prior Publication Data
US 2023/0012213 A1 Jan. 12, 2023

Related U.S. Application Data

(60) Provisional application No. 62/925,051, filed on Oct. 23, 2019.

(51) Int. Cl.
*C07K 16/32* (2006.01)
*A61K 47/68* (2017.01)

(52) U.S. Cl.
CPC ........ *C07K 16/32* (2013.01); *A61K 47/68031* (2023.08); *A61K 47/6855* (2017.08); *A61K 47/6879* (2017.08); *C07K 2317/24* (2013.01); *C07K 2317/31* (2013.01)

(58) Field of Classification Search
None
See application file for complete search history.

(56) References Cited

U.S. PATENT DOCUMENTS

| | | | |
|---|---|---|---|
| 4,737,456 A | 4/1988 | Weng et al. | |
| 4,816,567 A | 3/1989 | Cabilly et al. | |
| 4,965,343 A | 10/1990 | Felix et al. | |
| 5,641,870 A | 6/1997 | Rinderknecht et al. | |
| 5,849,954 A | 12/1998 | Carpino et al. | |
| 8,252,902 B2 | 8/2012 | Barbas et al. | |
| 8,604,025 B2 | 12/2013 | Morgan et al. | |
| 2009/0304721 A1 | 12/2009 | Kinch et al. | |
| 2010/0021379 A1 | 1/2010 | Lam et al. | |
| 2017/0112878 A1* | 4/2017 | Kaufmann | A61K 40/4276 |
| 2018/0250415 A1 | 9/2018 | Rader et al. | |

FOREIGN PATENT DOCUMENTS

| WO | WO-2014/144878 A2 | 9/2014 |
|---|---|---|
| WO | WO-2017/049139 A2 | 3/2017 |

OTHER PUBLICATIONS

International Search Report and Written Opinion for International Application No. PCT/US2020/055768, dated Oct. 15, 2020, (13 pages), U.S. Patent and Trademark Office, US.
Rader, Christoph et al. "A Humanized Aldolase Antibody For Selective Chemotherapy and Adaptor Immunotherapy," *Journal Of Molecular Biology*, vol. 332, No. 4, Sep. 26, 2003, pp. 889-899.
Yurkovetskly, Alexander V. et al. "A Polymer-Based Antibody-Vinca Drug Conjugate Platform: Characterization and Preclinical Efficacy," *Cancer Research*, vol. 75, Issue 16, Aug. 15, 2015, pp. 3365-3372, DOI: 10.1158/0008-5472.CAN-15-0129.
Presta, Leonard G. "Antibody Engineering," *Current Opinion in Structural Biology*, vol. 2, Issue 4, Aug. 1992, pp. 593-596.
Zhang, Chi et al. "Arylation Chemistry For Bioconjugation," *Angewandte Chemie International Edition*, vol. 58, No. 15, Apr. 1, 2019, pp. 4810-4839, DOI: 10.1002/anie.201806009.
Mitsunaga, Makoto et al. "Cancer Cell-Selective In Vivo Near Infrared Photoimmunotherapy Targeting Specific Membrane Molecules," *Nature Medicine*, vol. 17, No. 12, Dec. 2011, pp. 1685-1691, (ePub: Nov. 6, 2011), DOI: 10.1038/nm.2554.
Rader, Christoph et al. "Chemically Programmed Antibodies," *Trends Biotechnology*, vol. 32, No. 4, Apr. 2014, pp. 186-197, DOI: 10.1016/j.tibtech.2014.02.003.
Rader, Christoph et al. "Chemically Programmed Monoclonal Antibodies For Cancer Therapy: Adaptor Immunotherapy Based On A Covalent Antibody Catalyst," *Proceedings of the National Academy of Sciences*, vol. 100, No. 9, Apr. 20, 2003 pp. 5396-5400.
Morrison, Sherie L. et al. "Chimeric Human Antibody Molecules—Mouse Antigen-Binding Domains With Human Constant Region Domains," *Proceedings of the National Academy of Sciences*, Nov. 1984, vol. 81 No. 21, pp. 6851-6855.
Köhler, G. et al. "Continuous Cultures of Fused Cells Secreting Antibody of Predefined Specifity," *Nature*, vol. 256, Aug. 7, 1975, pp. 495-497.
Wagner, Jürgen et al. "Efficient Aldolase Catalytic Antibodies That Use The Enamine Mechanism of Natural Enzymes," *Science*, vol. 270, No. 5243, Dec. 15, 1995, pp. 1797-1800.
Nanna, Alex R. et al. "Engineering Dual Variable Domains For The (Continued)

*Primary Examiner* — Brad Duffy
(74) *Attorney, Agent, or Firm* — Alston & Bird LLP

(57) ABSTRACT

The present invention provides modified catalytic antibody 38C2 with arylation of the reactive lysine residue (Lys99). The Lys99 residue is arylated with a heteroaryl methyl sulfonyl compound such as methylsulfone phenyl oxadiazole (MS-PODA). The invention also provides antibody conjugated agents (e.g., antibody drug conjugates) that contain an agent moiety that is site-specifically conjugated to 38C2 via a methyl sulfonyl compound. Further provided in the invention are methods of making the antibody conjugated agents and therapeutic applications of the antibody conjugated agents.

18 Claims, 26 Drawing Sheets

Specification includes a Sequence Listing.

(56) References Cited

OTHER PUBLICATIONS eneration Of Site-Specific Antibody-Drug Conjugates," In *Massa, S., Devoogdt, N. (eds) Bioconjugation. Methods in Molecular Biology*, vol. 2033, Jul. 23, 2019, pp. 39-52, DOI: 10.1007/978-1-4939-9654-4_4.

Zapata, Gerardo et al. "Engineering Linear F(ab')2 Fragments For Efficient Production In *Escherichia coli* and Enhanced Antiproliferative Activity," Protein Engineering, Design and Selection, vol. 8, No. 10, Oct. 1, 1995, pp. 1057-1062, DOI: 10.1093/protein/8.10.1057.

Nanna, Alex R. et al. "Harnessing A Catalytic Lysine Residue For The One-Step Preparation of Homogeneous Antibody-Drug Conjugates," *Nature Communications*, vol. 8, No. 1112, Oct. 24, 2017, pp. 1-9, DOI: 10.1038/s41467-017-01257-1.

Barbas III, Carlos F. et al. "Immune Versus Natural Selection—Antibody Aldolases With Enzymic Rates But Broader Scope," *Science*, vol. 278, No. 5346, Dec. 19, 1997, pp. 2085-2092.

Patterson, James T. et al. "Improving The Serum Stability Of Site-Specific Antibody Conjugates With Sulfone Linkers," *Bioconjugate Chemistry*, vol. 25, No. 8, Aug. 6, 2014, pp. 1402-1407.

Toda, Narihiro et al. "Rapid, Stable, Chemoselective Labeling Of Thiols With Julia-Kocienski-Like Reagents: A Serum-Stable Alternative To Maleimide-Based Protein Conjugation," *Angewandte Chemie International Edition In English*, vol. 52, No. 48, Nov. 25, 2013, (ePub: Oct. 2, 2013), pp. 12592-12596, DOI: 10.1002/anie.201306241.

Jones, Peter T. et al. "Replacing The Complementarity-Determining Regions In A Human Antibody With Those From A Mouse," *Nature Publishing Group*, vol. 321, No. 6069, May 19, 1986, pp. 522-525.

Riechmann, L. et al. "Reshaping Human Antibodies For Therapy," *Nature*, Mar. 24, 1988 Mar, vol. 332, No. 6162, pp. 323-327.

Hwang, Dobeen et al. "Site-Selective Antibody Functionalization via Orthogonally Reactive Arginine and Lysine Residues," *Cell Chemical Biology*, vol. 26, Sep. 19, 2019, pp. 1229-1239, DOI: 10.1016/j.chembiol.2019.05.010.

Hwang, Dobeen et al. "Site-Specific Lysine Arylation As An Alternative Bioconjugation Strategy For Chemically Programmed Antibodies and Antibody-Drug Conjugates," *Bioconjugate Chemistry*, vol. 30, No. 11, Nov. 1, 2019, pp. 2889-2896, DOI: 10.1021/acs.bioconjchem.9b00609.

Beck, Alain et al. "Strategies And Challenges For The Next Generation Of Antibody-Drug Conjugates," *Nature Reviews Drug Discovery*, vol. 16, Mar. 17, 2017, pp. 315-317, (ePub: Mar. 17, 2017), DOI: 10.1038/nrd.2016.268.

Plückthun, A. "Antibodies From *Escherichia coli*," Pharmacology of Monoclonal Antibodies, Rosenburg and Moore eds., Springer-Verlag, New York, (Year: 1994), vol. 113, Chapter 11, pp. 269-315.

Matos, Maria et al., "Chemo- and Regioselective Lysine Modification on Native Proteins", *Journal of the American Chemical Society*, vol. 140, No. 11, Mar. 21, 2018, pp. 4004-4017, doi:10.1021/jacs.7612874.

Extended European Search Report for European Application No. 20879521.1, dated Jul. 5, 2024, 12 pages.

Narihiro, Toda, et al., "Rapid, Stable, Chemoselective Labeling of Thiols with Julia-Kocienskiń ski-like Reagents: A Serum-Stable Alternative to Maleimide-Based Protein Conjugation", *Angewandte Chemie International Edition*, vol. 52, No. 48, Nov. 25, 2013, pp. 12592-12596, doi: 10.1002/anie.201306241.

Protein Data Bank in Europe, "Site-specific Lysine Arylation as an Alternative Bioconjugation Strategy for Chemically Programmed Antibodies and Antibody-drug Conjugates", Nov. 13, 2019, (3 pages), doi: 10.2210/pdb6u85/pdb.

\* cited by examiner

FIG. 4A

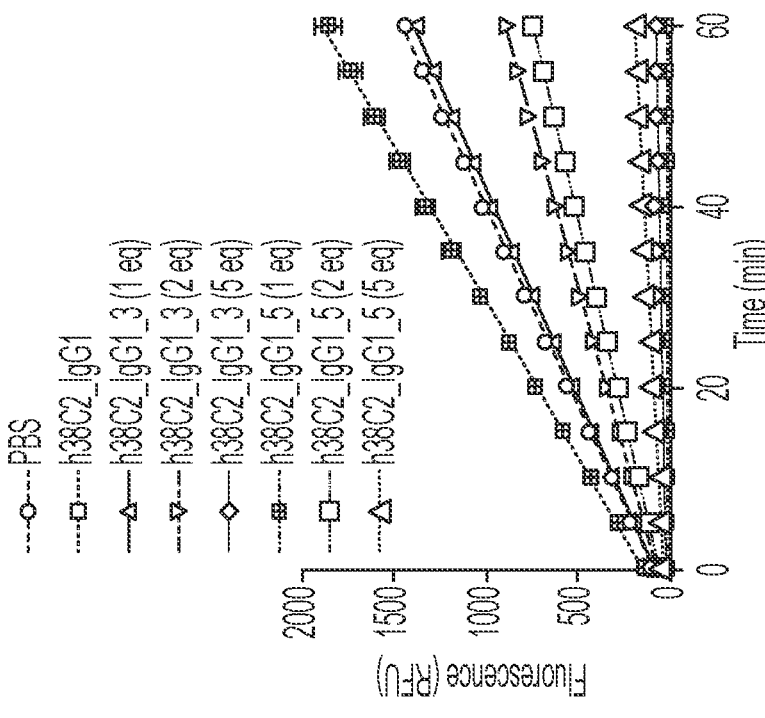
FIG. 4B
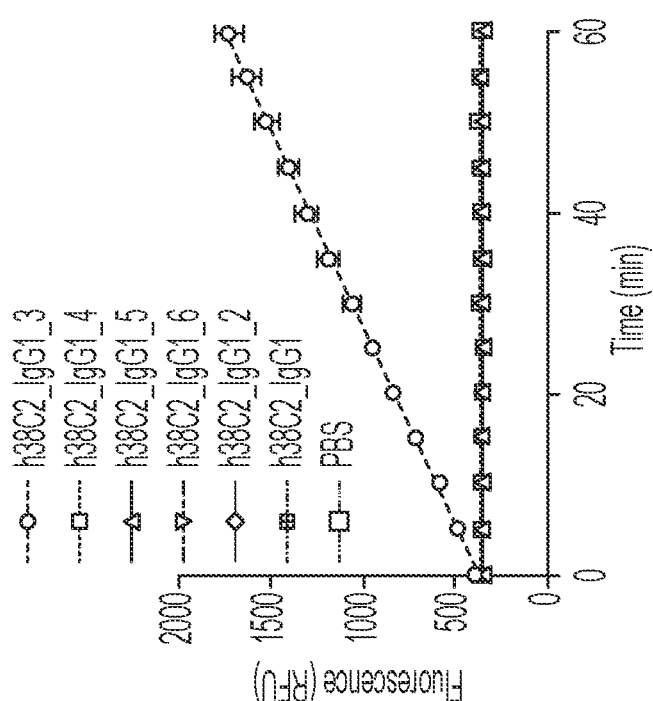

KPL-4

Figure 10A

16: R = Folate
17: R = LLP2A

3: R = Folate
4: R = LLP2A

Figure 11A

SEQUENCE LISTING

<160> NUMBER OF SEQ ID NOS: 4

<210> SEQ ID NO 1
<211> LENGTH: 112
<212> TYPE: PRT
<213> ORGANISM: Artificial sequence
<220> FEATURE:
<223> OTHER INFORMATION: Synthesized

<400> SEQUENCE: 1

```
Asp Val Val Met Thr Gln Thr Pro Leu Ser Leu Pro Val Arg Leu Gly
1               5                   10                  15

Asp Gln Ala Ser Ile Ser Cys Arg Ser Ser Gln Ser Leu Leu His Thr
            20                  25                  30
```

-continued

```
Tyr Gly Ser Pro Tyr Leu Asn Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Arg Ile
65                  70                  75                  80

Ser Arg Val Glu Ala Glu Asp Leu Gly Val Tyr Phe Cys Ser Gln Gly
                85                  90                  95

Thr His Leu Pro Tyr Thr Phe Gly Gly Gly Thr Lys Leu Glu Ile Lys
            100                 105                 110

<210> SEQ ID NO 2
<211> LENGTH: 118
<212> TYPE: PRT
<213> ORGANISM: Artificial sequence
<220> FEATURE:
<223> OTHER INFORMATION: Synthesized

<400> SEQUENCE: 2

Glu Val Lys Leu Val Glu Ser Gly Gly Gly Leu Val Gln Pro Gly Gly
1               5                   10                  15

Thr Met Lys Leu Ser Cys Glu Ile Ser Gly Leu Thr Phe Arg Asn Tyr
            20                  25                  30

Trp Met Ser Trp Val Arg Gln Ser Pro Glu Lys Gly Leu Glu Trp Val
        35                  40                  45

Ala Glu Ile Arg Leu Arg Ser Asp Asn Tyr Ala Thr His Tyr Ala Glu
    50                  55                  60

Ser Val Lys Gly Lys Phe Thr Ile Ser Arg Asp Asp Ser Lys Ser Arg
65                  70                  75                  80

Leu Tyr Leu Gln Met Asn Ser Leu Arg Thr Glu Asp Thr Gly Ile Tyr
                85                  90                  95

Tyr Cys Lys Thr Tyr Phe Tyr Ser Phe Ser Tyr Trp Gly Gln Gly Thr
            100                 105                 110

Leu Val Thr Val Ser Ala
        115

<210> SEQ ID NO 3
<211> LENGTH: 112
<212> TYPE: PRT
<213> ORGANISM: Artificial sequence
<220> FEATURE:
<223> OTHER INFORMATION: Synthesized

<400> SEQUENCE: 3

Glu Leu Gln Met Thr Gln Ser Pro Ser Ser Leu Ser Ala Ser Val Gly
1               5                   10                  15

Asp Arg Val Thr Ile Thr Cys Arg Ser Ser Gln Ser Leu Leu His Thr
            20                  25                  30

Tyr Gly Ser Pro Tyr Leu Asn Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Ser Arg Phe Ser Gly Ser Gly Ser Gly Thr Asp Phe Thr Leu Thr Ile
65                  70                  75                  80

Ser Ser Leu Gln Pro Glu Asp Phe Ala Val Tyr Phe Cys Ser Gln Gly
                85                  90                  95

Thr His Leu Pro Tyr Thr Phe Gly Gly Gly Thr Lys Val Glu Ile Lys
```

-continued

```
         100              105              110
```

```
<210> SEQ ID NO 4
<211> LENGTH: 118
<212> TYPE: PRT
<213> ORGANISM: Artificial sequence
<220> FEATURE:
<223> OTHER INFORMATION: Synthesized

<400> SEQUENCE: 4

Glu Val Gln Leu Val Glu Ser Gly Gly Gly Leu Val Gln Pro Gly Gly
1               5                  10                  15

Ser Leu Arg Leu Ser Cys Ala Ala Ser Gly Phe Thr Phe Ser Asn Tyr
            20                  25                  30

Trp Met Ser Trp Val Arg Gln Ser Pro Glu Lys Gly Leu Glu Trp Val
        35                  40                  45

Ser Glu Ile Arg Leu Arg Ser Asp Asn Tyr Ala Thr His Tyr Ala Glu
    50                  55                  60

Ser Val Lys Gly Arg Phe Thr Ile Ser Arg Asp Asn Ser Lys Asn Thr
65                  70                  75                  80

Leu Tyr Leu Gln Met Asn Ser Leu Arg Ala Glu Asp Thr Gly Ile Tyr
                85                  90                  95

Tyr Cys Lys Thr Tyr Phe Tyr Ser Phe Ser Tyr Trp Gly Gln Gly Thr
            100                 105                 110

Leu Val Thr Val Ser Ser
            115
```

CONJUGATION CHEMISTRY FOR CATALYTIC ANTIBODY 38C2

CROSS-REFERENCE TO RELATED APPLICATIONS

The subject patent application is a national phase entry of PCT/US2020/055768 (filed Oct. 15, 2020), which claims the benefit of priority to U.S. Provisional Patent Application No. 62/925,051 (filed Oct. 23, 2019). The full disclosure of the priority application is incorporated herein by reference in its entirety and for all purposes.

STATEMENT OF GOVERNMENT SUPPORT

This invention was made with government support under grant number CA174844 awarded by the National Institutes of Health. The government has certain rights in the invention.

REFERENCE TO AN ELECTRONIC SEQUENCE LISTING

The contents of the electronic sequence listing (575639SEQLST.TXT; Size: 4.6 KB; and Date of Creation Dec. 2, 2025), is herein incorporated by reference in its entirety.

BACKGROUND OF THE INVENTION

Antibody-small molecule conjugates are broadly used in basic research and for the diagnosis and therapy of diseases. For example, Food and Drug Administration (FDA)-approved and currently marketed therapeutic antibody-small molecule conjugates include five antibody-drug conjugates and one radioimmunoconjugate. Although none of these assemble antibody and small molecule by site-specific bioconjugation strategies, the recent utilization of natural or engineered uniquely reactive amino acids or carbohydrates affords highly homogeneous antibody-small molecule conjugates. By facilitating the manufacture and application of molecularly defined assemblies of antibody-small molecule conjugates, they have become state-of-the-art reagents backed by a rich preclinical and clinical pipeline.

Based on a uniquely reactive lysine residue (Lys99) in its active site, the catalytic antibody 38C2 and its humanized version h38C2 have been used as bioconjugation modules for the assembly of highly homogeneous antibody-small molecule conjugates. Lys99 lies at the bottom of a deep hydrophobic pocket. Unlike surface Lys residues, it is deprotonated at physiological pH and highly nucleophilic. This has been harnessed for the site-specific covalent conjugation of small molecules that are derivatized with an electrophilic β-diketone or β-lactam group, which form enaminone or amide adducts, respectively, with the ε-amino group of the buried Lys99 residue. Chemically programmed antibodies that utilize h38C2 as a bioconjugation module to endow small molecules with the pharmacokinetic and pharmacodynamic properties of monoclonal antibodies (mAbs), have been investigated in phase I and II clinical trials. Furthermore, T-cell engaging bispecific antibodies have been equipped with h38C2 bioconjugation modules to link small molecules that target cell surface receptors to the power of immunotherapy. Finally, dual variable domain (DVD)-based antibody-drug conjugates (ADCs) have used h38C2 as a bioconjugation module for the rapid, precise, efficient and stable conjugation of highly cytotoxic payloads under mild conditions.

Nevertheless, there is still an unmet need for alternative and better means for antibody conjugation with smaller agents or molecules. The present invention is directed to this and other needs in the art.

SUMMARY OF THE INVENTION

In one aspect, the invention provides modified or functionalized catalytic antibody 38C2 molecules. In these variant antibodies, the reactive lysine residue Lys99 is arylated. Preferably, the variant 38C2 antibody is derived from humanized 38C2 (h38C2). Typically, the Lys99 residue is arylated with a heteroaryl methylsulfonyl compound. In some embodiments, the heteroaryl methylsulfonyl compound used for the arylation is methylsulfone phenyloxadiazole (MS-PODA).

In another aspect, the invention provides antibody-agent conjugate compounds. These compounds contain an agent moiety that is conjugated to the reactive residue Lys99 of an 38C2 antibody via a heteroaryl methylsulfonyl compound linker. Preferably, the catalytic antibody 38C2 for making the antibody-agent conjugates is humanized 38C2. In some embodiments, the employed 38C2 antibody is IgG1 or Fab. In some embodiments, the agent moiety is derivatized with the heteroaryl methylsulfonyl compound prior to conjugation to antibody 38C2. In some of these embodiments, the heteroaryl methylsulfonyl compound for derivatizing the agent moiety is methylsulfone phenyloxadiazole (MS-PODA).

In some embodiments, the agent moiety in the conjugate compounds is a drug moiety or a cytotoxic agent. In some of these embodiments, the drug moiety in the conjugates is MMAF. In some other antibody-agent conjugates of the invention, the agent moiety is a targeting moiety. In some of these embodiments, the targeting moiety is folate or LLP2A.

Some antibody-agent conjugates of the invention are dual variable domain antibody drug conjugates (DVD-ADCs). In some of these embodiments, the second variant domain specifically targets a tumor antigen or marker (e.g., HER2).

In some related embodiments, the invention provides pharmaceutical compositions that contain an effective amount of an antibody-agent conjugate described herein and optionally a pharmaceutically acceptable carrier. In some other embodiments, the invention provides methods for treating cancer in a subject. The methods entail administering to a subject in need of treatment a pharmaceutical composition of the invention. The antibody-agent conjugate in the pharmaceutical compositions for use in these methods can be a tumor targeting DVD antibody drug compound, an antibody-agent conjugate wherein the agent is a drug moiety or a cytotoxic molecule, or a chemically programmed antibody described herein.

In another aspect, the invention provides method for conjugating an agent to catalytic antibody 38C2. The methods involve (a) reacting the agent with a heteroaryl methylsulfonyl compound to generate a derivatized agent, and (b) reacting the derivatized agent with catalytic antibody 38C2; thereby conjugating the agent to catalytic antibody 38C2. In some methods, the employed agent is a drug moiety or a targeting moiety. In some of these methods, the agent is a small molecule agent or a nucleic acid agent.

A further understanding of the nature and advantages of the present invention may be realized by reference to the remaining portions of the specification and claims.

DESCRIPTION OF THE DRAWINGS

FIG. 4. Chemical programming of h38C2 IgG1. (A) Structures of the (3-lactam hapten derivatives of folate (compound 3) and LLP2A (compound 4) and structures of the MS-PODA derivatives of folate (compound 5) and LLP2A (compound 6) used in this study. (B) (left) Catalytic activity of h38C2 IgG1 (1 μM) before and after conjugation to 5 equiv of compounds 2-6 (mean±SD of triplicates). (right) Catalytic activity of h38C2 IgG1 (1 μM) before and after conjugation to 1, 2, and 5 equiv of compounds 3 and 5 (mean±SD of triplicates).

FIGS. 10A-10C. 10A. Scheme 2. Synthesis of azido peptides targeting either FOLR1 (16) or integrin $\alpha_4\beta_1$ (17). (a) Fmoc-SPPS; (b) Fmoc-L-Glu(OH)-Ot-Bu, HATU, DIEA, NMP then 20% (v/v) piperidine in DMF; (c) N-10-TFA-pteroic acid, HATU, DIEA, NMP; (d) 2% (v/v) hydrazine monohydrate in NMP; (e) azidoacetic acid NHS ester, DIEA, NMP; (f) TFA/TIPS/H$_2$O=95:2.5:2.5; (g) Fmoc-SPPS using Fmoc-Ach-OH, Fmoc-L-Aad(Ot-Bu)-OH, and Fmoc-L-Lys(Alloc)-OH; (h) MPUPA-NHS ester, DIEA, NMP; (i) Pd(PPh$_3$)$_4$, PhSiH$_3$, CHCl$_3$; (j) trans-3-(3-pyridyl)-acrylic acid, HATU, DIEA, NMP; (k) 2% (v/v) hydrazine monohydrate in NMP, allyl alcohol. 10B. Chromatogram 1. Analytical HPLC of azido-folate peptide 16. 10C. Chromatogram 2. Analytical HPLC of azido-LLP2A peptide 17.

FIGS. 11A-11C. 11A. Scheme 3. Synthesis of β-lactam-hapten-folate 3 and β-lactam-hapten-LLP2A 4. (a) 14, $CuSO_4 \cdot 5H_2O$, TBTA, sodium ascorbate, $DMSO/H_2O=1:1$, 54% for 3 and 66% for 4. 11B. Chromatogram 3. Analytical HPLC of β-lactam-hapten-folate 3. 11C. Chromatogram 4. Analytical HPLC of β-lactam-hapten-LLP2A 4.

DETAILED DESCRIPTION

Figure 1A:
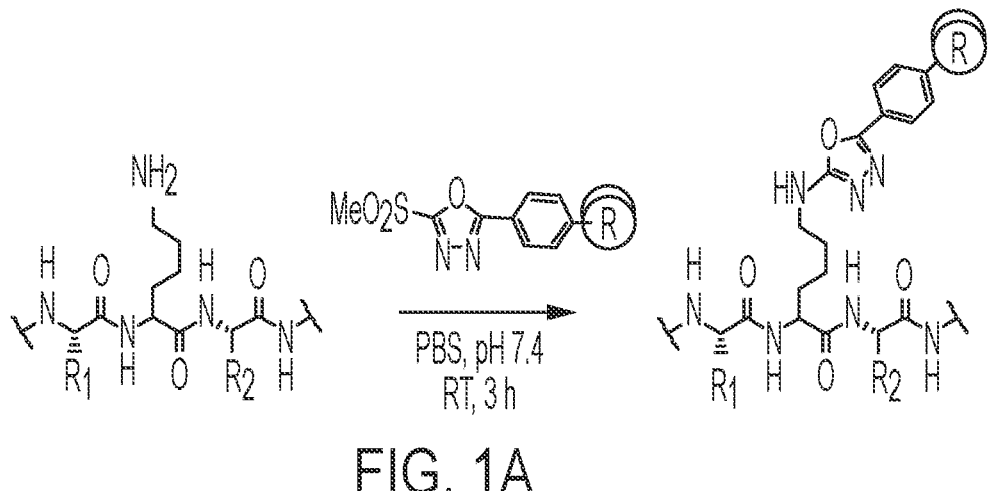
FIG. 1. Heteroarylation of the reactive Lys residue of catalytic antibody h38C2. (A) Proposed reaction of MS-PODA with the ε-amino group of Lys99 under mild conditions. The side chains of the flanking Cys and threonine (Thr) residues are shown as R1 and R2, respectively. (B) In silico docking model of PODA-conjugated Lys99 in the hydrophobic pocket (box) of h38C2. The Fab's heavy chain (VH-CH1) is shown in blue, and the light chain (VL-CL) is in green. Interatomic distances (given in A) were calculated by PyMOL software.

By exploiting a uniquely reactive lysine residue (Lys99) for site-specific attachment of small molecules, the humanized catalytic antibody h38C2 has been used as bioconjugation module in the assembly of chemically programmed antibodies and antibody-drug conjugates. Treatment of h38C2 with β-lactam-functionalized small molecules has been previously shown to result in covalent conjugation by selective formation of a stable amide bond with the ε-amino group of the Lys99 residue.

The present invention is derived in part from studies undertaken by the inventors to investigate alternative conjugation chemistry with the objective of providing additional options for payload derivatization. As detailed herein, the inventors employed heteroaryl methylsulfones to functionalize drugs or small molecule compounds for conjugating to h38C2, and examined whether such an alternative conjugation chemistry affords higher serum stability compared to conventional maleimide conjugation. The inventors hypothesized that the ε-amino group of the buried Lys99 residue of h38C2 and heteroaryl methylsulfone-functionalized small molecules present a compatible electron-pair donor/acceptor system. Accordingly, the inventors analyzed the efficiency, site-specificity, and stability of such bioconjugates. Chemically programmed antibodies and ADCs generated by Lys arylation using methylsulfone oxadiazole derivatives and by Lys amidation using β-lactam derivatives were directly compared in functional assays. As exemplified herein with conjugation of folate, LLP2A and MMAF, these studies demonstrated the practicality, versatility, and utility of this alternative bioconjugation strategy.

Currently, all therapeutic utilities of h38C2 for (i) chemically programmed antibodies, bispecific antibodies, and chimeric antigen receptors and (ii) antibody-drug conjugates and antibody-siRNA conjugates require β-lactam hapten-based conjugation. By providing an alternative conjugation chemistry, the invention further increases the accessible payload space. For example, payloads that are incompatible with the β-lactam hapten-based conjugation chemistry may be compatible with a heteroaryl methylsulfonyl functionality.

Before the present invention is described in greater detail, it is to be understood that this invention is not limited to particular aspects described, as such may, of course, vary. It is also to be understood that the terminology used herein is for the purpose of describing particular aspects only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

Certain ranges are presented herein with numerical values being preceded by the term "about." The term "about" is used herein to provide literal support for the exact number that it precedes, as well as a number that is near to or approximately the number that the term precedes. In determining whether a number is near to or approximately a specifically recited number, the near or approximating unrecited number may be a number which, in the context in which it is presented, provides the substantial equivalent of the specifically recited number.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed.

The practice of the present invention can employ, unless otherwise indicated, conventional techniques of molecular biology (including recombinant techniques), microbiology, cell biology, biochemistry, and immunology, which are within the skill of the art. Such techniques are explained fully in the literature. See, e.g., Methods in Enzymology, Volume 289: *Solid-Phase Peptide Synthesis*, J. N. Abelson, M. I. Simon, G. B. Fields (Editors), Academic Press; 1st edition (1997) (ISBN-13: 978-0121821906); U.S. Pat. Nos. 4,965,343, and 5,849,954; Sambrook et al., *Molecular Cloning: A Laboratory Manual*, Cold Spring Harbor Press, N.Y., ($3^{rd}$ ed., 2000); Brent et al., *Current Protocols in Molecular Biology*, John Wiley & Sons, Inc. (ringbou ed., 2003); Barbas et al., *Phage Display: A Laboratory Manual*, CSHL Press (2004); Davis et al., *Basic Methods in Molecular Biology*, Elsevier Science Publishing, Inc., New York, USA (1986); *Methods in Enzymology: Guide to Molecular Cloning Techniques*, Vol. 152, S. L. Berger and A. R. Kimmerl Eds., Academic Press Inc., San Diego, USA (1987); *Current Protocols in Protein Science* (CPPS) (John E. Coligan, et. al., ed., John Wiley and Sons, Inc.); *Current Protocols in Cell Biology* (CPCB) (Juan S. Bonifacino et. al. ed., John Wiley and Sons, Inc.); *Culture of Animal Cells: A Manual of Basic Technique and Specialized Applications*, R. Ian Freshney, Wiley Blackwell (7th edition, 2015); and *Animal Cell*

*Culture Methods*, Jennie P. Mather and David Barnes editors, Academic Press ($1^{st}$ edition, 1998). The following sections provide additional guidance for practicing the compositions and methods of the present invention.

As will be apparent to those of skill in the art upon reading this disclosure, each of the individual aspects described and illustrated herein has discrete components and features which can be readily separated from or combined with the features of any of the other several aspects without departing from the scope or spirit of the present invention. Any recited method can be carried out in the order of events recited or in any other order which is logically possible. Although any methods and materials similar or equivalent to those described herein can also be used in the practice or testing of the present invention, representative illustrative methods and materials are now described.

Unless defined otherwise, all technical and scientific terms used herein have the same meaning as commonly understood by those of ordinary skill in the art to which this invention pertains. The following references provide one of skill with a general definition of many of the terms used in this invention: *Academic Press Dictionary of Science and Technology*, Morris (Ed.), Academic Press (1st ed., 1992); *Oxford Dictionary of Biochemistry and Molecular Biology*, Smith et al. (Eds.), Oxford University Press (revised ed., 2000); *Encyclopaedic Dictionary of Chemistry*, Kumar (Ed.), Anmol Publications Pvt. Ltd. (2002); *Dictionary of Microbiology and Molecular Biology*, Singleton et al. (Eds.), John Wiley & Sons ($3^{rd}$ ed., 2002); *Dictionary of Chemistry*, Hunt (Ed.), Routledge (1st ed., 1999); *Dictionary of Pharmaceutical Medicine*, Nahler (Ed.), Springer-Verlag Telos (1994); *Dictionary of Organic Chemistry*, Kumar and Anandand (Eds.), Anmol Publications Pvt. Ltd. (2002); and *A Dictionary of Biology* (*Oxford Paperback Reference*), Martin and Hine (Eds.), Oxford University Press ($4^{th}$ ed., 2000). Further clarifications of some of these terms as they apply specifically to this invention are provided herein.

It is noted that, as used herein and in the appended claims, the singular forms "a", "an", and "the" include plural referents unless the context clearly dictates otherwise. It is further noted that the claims can be drafted to exclude any optional element. As such, this statement is intended to serve as antecedent basis for use of such exclusive terminology as "solely," "only" and the like in connection with the recitation of claim elements, or use of a "negative" limitation.

The term "immunoglobulin" or "antibody" as used interchangeably herein refers to a basic 4-chain heterotetrameric glycoprotein composed of two identical light (L) chains and two identical heavy (H) chains. Each L chain is linked to an H chain by one covalent disulfide bond, while the two H chains are linked to each other by one or more disulfide bonds depending on the H chain isotype. Each H and L chain has an N-terminus and a C-terminus, and also has regularly spaced intrachain disulfide bridges. Each H chain has at the N-terminus a variable domain ($V_H$) followed by three constant domains ($C_H1$, $C_H2$ and $C_H3$). Each L chain has at the N-terminus a variable domain ($V_L$) followed by one constant domain ($C_L$). The $V_L$ is aligned with the $V_H$ and the $C_L$ is aligned with the first constant domain of the heavy chain ($C_H1$). Particular amino acid residues are believed to form an interface between the L chain and H chain variable domains. The pairing of a $V_H$ and $V_L$ together forms a single antigen-binding site.

The L chain from any vertebrate species can be assigned to one of two clearly distinct types, called kappa and lambda, based on the amino acid sequences of their constant domains. Depending on the amino acid sequence of the constant domain of their heavy chains ($C_H$), immunoglobulins can be assigned to different classes or isotypes. There are five classes of immunoglobulins: IgA, IgD, IgE, IgG, and IgM, having heavy chains designated α, δ, ε, γ, and μ, respectively. The γ and α classes are further divided into subclasses on the basis of relatively minor differences in $C_H$ sequence and function, e.g., humans express the following subclasses: IgG1, IgG2, IgG3, IgG4, IgA1, and IgA2.

The "variable region" or "variable domain" of an immunoglobulin refers to the N-terminal domains of the H or L chain of the immunoglobulin. The variable domain of the H chain can be referred to as "$V_H$." The variable domain of the light chain can be referred to as "$V_L$." These domains are generally the most variable parts of an immunoglobulin and contain the antigen-binding sites.

The term "variable" refers to the fact that certain segments of the variable domains differ extensively in sequence among immunoglobulins. The V domain mediates antigen binding and defines specificity of a particular immunoglobulin for its particular antigen. However, the variability is not evenly distributed across the 110-amino acid span of most variable domains. Instead, the V regions consist of relatively invariant stretches called framework regions (FRs) of 15-30 amino acids separated by shorter regions of extreme variability called "hypervariable regions" that are each 9-12 amino acids long. The variable domains of native H and L chains each comprise four FRs, largely adopting a 3-sheet configuration, connected by three hypervariable regions, which form loops connecting, and in some cases forming part of, the 3-sheet structure. The hypervariable regions in each chain are held together in close proximity by the FRs and, with the hypervariable regions from the other chain, contribute to the formation of the antigen-binding site of immunoglobulins (see Kabat et al., Sequences of Proteins of Immunological Interest, 5th Ed. Public Health Service, National Institutes of Health, Bethesda, MD (1991)). The constant domains are not involved directly in binding an immunoglobulin to an antigen, but exhibit various effector functions, such as participation of the immunoglobulin in antibody dependent cellular cytotoxicity (ADCC), antibody-dependent cellular phagocytosis (ADCP), and complement-dependent cytotoxicity (CDC).

An "intact" immunoglobulin is one that comprises an antigen-binding site as well as a $C_L$ and at least H chain constant domains, $C_H1$, $C_H2$ and $C_H3$. The constant domains can be native sequence constant domains (e.g., human native sequence constant domains) or amino acid sequence variants thereof. An intact immunoglobulin can have one or more effector functions.

A "naked immunoglobulin" for the purposes herein is an immunoglobulin that is not conjugated to a drug moiety.

"Immunoglobulin fragments" comprise a portion of an intact immunoglobulin, preferably the antigen binding or variable region of the intact immunoglobulin. Examples of immunoglobulin fragments include, but are not limited to, Fab, Fab', F(ab')$_2$, and Fv fragments; diabodies; linear immunoglobulins (see U.S. Pat. No. 5,641,870, Example 2; Zapata et al., Protein Eng. 8(10): 1057-1062 [1995]); single-chain immunoglobulin molecules; and multispecific immunoglobulins formed from immunoglobulin fragments. In some embodiments, the immunoglobulin fragments include all possible alternate fragment formats. In some embodiments, the immunoglobulin fragments may be bispecific. In some embodiments, the immunoglobulin fragments may be bi-paratopic. In some embodiments, the immunoglobulin fragments may be trispecific. In some embodiments, the immunoglobulin fragments may be multimeric. In some embodiments, an immunoglobulin fragment comprises an antigen binding site of the intact immunoglobulin and thus retains the ability to bind antigen. In some embodiments, the immunoglobulin fragment contains single variable domains which have the ability to bind antigen. In some embodiments, the immunoglobulin fragments are further modified (not limited to peptide addition, pegylation, hesylation, glycosylation) to modulate activity, properties, pharmacokinetic behavior and in vivo efficacy.

Papain digestion of immunoglobulins produces two identical antigen-binding fragments, called "Fab" fragments, and a residual "Fc" fragment, a designation reflecting the ability to crystallize readily. The Fab fragment consists of an entire L chain along with the variable region domain of the H chain ($V_H$), and the first constant domain of one heavy chain ($C_H1$). Each Fab fragment is monovalent with respect to antigen binding, i.e., it has a single antigen-binding site. Pepsin treatment of an immunoglobulin yields a single large $F(ab')_2$ fragment which roughly corresponds to two disulfide linked Fab fragments having divalent antigen-binding activity and is still capable of cross-linking antigen. Fab' fragments differ from Fab fragments by having additional few residues at the carboxy terminus of the $C_H1$ domain including one or more cysteines from the immunoglobulin hinge region. Fab'-SH is the designation herein for Fab' in which the cysteine residue(s) of the constant domains bear a free thiol group. $F(ab')_2$ immunoglobulin fragments originally were produced as pairs of Fab' fragments which have hinge cysteines between them. Other chemical couplings of immunoglobulin fragments are also known.

The Fc fragment comprises the carboxy-terminal portions of both H chains held together by disulfides. The effector functions of immunoglobulins are determined by sequences in the Fc region, which region is also the part recognized by Fc receptors (FcR) found on certain types of cells.

"Fv" is the minimum immunoglobulin fragment which contains a complete antigen-recognition and -binding site. This fragment consists of a dimer of one heavy- and one light-chain variable region domain in tight, non-covalent association. In a single-chain Fv (scFv) species, one heavy- and one light-chain variable domain can be covalently linked by a flexible peptide linker such that the light and heavy chains can associate in a "dimeric" structure analogous to that in a two-chain Fv species. From the folding of these two domains emanate six hypervariable loops (3 loops each from the H and L chain) that contribute the amino acid residues for antigen binding and confer antigen binding specificity to the immunoglobulin. However, even a single variable domain (or half of an Fv comprising only three CDRs specific for an antigen) has the ability to recognize and bind antigen, although typically at a lower affinity than the entire binding site. When used herein in reference to a DVD immunoglobulin molecule, the term "Fv" refers to a binding fragment that includes both the first and the second variable domains of the heavy chain and the light chain.

"Single-chain Fv" also abbreviated as "sFv" or "scFv" are immunoglobulin fragments that comprise the $V_H$ and $V_L$ immunoglobulin domains connected into a single polypeptide chain. Preferably, the sFv polypeptide further comprises a polypeptide linker between the $V_H$ and $V_L$ domains which enables the sFv to form the desired structure for antigen binding. For a review of sFv, see Plückthun in *The Pharmacology of Monoclonal Antibodies*, vol. 113, Rosenburg and Moore eds., Springer-Verlag, New York, pp. 269-315 (1994); and *Antibody Engineering*, Borrebaeck ed., Oxford University Press (1995). When used herein in reference to a DVD immunoglobulin molecule, the term "scFv" refers to a binding fragment that includes both the first and the second variable domains of the heavy chain and the light chain.

As used herein, a "dual variable domain (DVD) compound" or a "dual variable domain (DVD) immunoconjugate" refers to compound that has a first and a second variable domain of immunoglobulins (include antigen-binding fragments of Ig such as Fab), and a drug moiety that is covalently conjugated to the second variable domain via a linker. The term "dual variable domain immunoglobulin" or "DVD-Ig" as used herein refers to an immunoglobulin molecule the H and L chains of which both include a second variable domain located adjacent to the first variable domain. The L chain of a DVD-Ig therefore includes, from N-terminus to C-terminus, the following domains: $V_L1$-$V_L2$-$C_L$. The H chain of a DVD-Ig therefore includes, from N-terminus to C-terminus, the following domains: $V_H1$-$V_H2$-$C_H1$-$C_H2$-$C_H3$. The pairing of a $V_L1$ and $V_H1$ together forms a first antigen-binding site. The pairing of a $V_L2$ and $V_H2$ together forms a second antigen binding site. In some embodiments, the DVD compound of the invention is DVD-Fab, which contains an immunoglobulin component that is an antigen binding fragment of Ig such as an Fab fragment. General methods of making various DVD compounds of the invention are described in the art, e.g., Nanna et al., Nat. Commun. 8:1112, 2017.

Unless stated otherwise, the term "immunoglobulin" or "antibody" specifically includes native human and non-human IgG1, IgG2, IgG3, IgG4, IgE, IgA1, IgA2, IgD and IgM antibodies, including naturally occurring variants.

The term "polypeptide" is used herein in the broadest sense and includes peptide sequences. The term "peptide" generally describes linear molecular chains of amino acids containing up to about 30, preferably up to about 60 amino acids covalently linked by peptide bonds.

The term "monoclonal" as used herein refers to an antibody or immunoglobulin molecule (e.g., a DVD Ig molecule) obtained from a population of substantially homogeneous immunoglobulins, i.e., the individual immunoglobulins comprising the population are identical except for possible naturally occurring mutations that can be present in minor amounts. Monoclonal immunoglobulins are highly specific, being directed against a single antigenic site. Furthermore, in contrast to conventional (polyclonal) antibody preparations which typically include different antibodies directed against different determinants (epitopes), each monoclonal immunoglobulin is directed against a single determinant on the antigen. The modifier "monoclonal" indicates the character of the immunoglobulin as being obtained from a substantially homogeneous population of immunoglobulins, and is not to be construed as requiring production of the antibody by any particular method. For example, the monoclonal immunoglobulins in accordance with the present invention can be made by the hybridoma method first described by Kohler and Milstein (1975) Nature 256:495, or can be made by recombinant DNA methods (see, e.g., U.S. Pat. No. 4,816,567).

The monoclonal immunoglobulins herein specifically include "chimeric" immunoglobulins in which a portion of the heavy and/or light chain is identical with or homologous to corresponding sequences in antibodies derived from a particular species, while the remainder of the chain(s) is identical with or homologous to corresponding sequences in antibodies derived from another species, as well as fragments of such antibodies, so long as they exhibit the desired biological activity (U.S. Pat. No. 4,816,567; and Morrison et al. (1984) Proc. Natl. Acad. Sci. USA 81:6851-6855).

"Humanized" forms of non-human (e.g., rodent, e.g., murine or rabbit) immunoglobulins are immunoglobulins which contain minimal sequences derived from non-human immunoglobulin. For the most part, humanized immunoglobulins are human immunoglobulins (recipient antibody) in which residues from a hypervariable region of the recipient are replaced by residues from a hypervariable region of a non-human species (donor antibody) such as mouse, rat, hamster, rabbit, chicken, bovine or non-human primate having the desired specificity, affinity, and capacity. In some instances, Fv framework region (FR) residues of the human immunoglobulin are also replaced by corresponding non-human residues. Furthermore, humanized antibodies can comprise residues which are not found in the recipient antibody or in the donor antibody. These modifications are made to further refine antibody performance. In general, the humanized immunoglobulin will comprise substantially all of at least one, and typically two, variable domains, in which all or substantially all of the hypervariable loops correspond to those of a non-human immunoglobulin and all or substantially all of the FR regions are those of a human immunoglobulin sequence. The humanized immunoglobulin optionally also will comprise at least a portion of an immunoglobulin constant region (Fc), typically that of a human immunoglobulin. For further details, see Jones et al. (1986) Nature 321:522-525; Riechmann et al. (1988) Nature 332:323-329; and Presta (1992) Curr. Op. Struct. Biol. 2:593-596.

The term "human immunoglobulin", as used herein, is intended to include immunoglobulins having variable and constant regions derived from human germline immunoglobulin sequences. The human immunoglobulins of the invention can include amino acid residues not encoded by human germline immunoglobulin sequences (e.g., mutations introduced by random or site-specific mutagenesis in vitro or by somatic mutation in vivo), for example in the CDRs and in particular CDR3. However, the term "human immunoglobulin", as used herein, is not intended to include immunoglobulins in which CDR sequences derived from the germline of another mammalian species, such as a mouse, have been grafted onto human framework sequences.

An "isolated" immunoglobulin herein is one which has been identified and separated and/or recovered from a component of its natural environment in a recombinant host cell. Contaminant components of its natural environment are materials which would interfere with diagnostic or therapeutic uses for the immunoglobulin, and can include enzymes, hormones, and other proteinaceous or nonproteinaceous solutes, as well as undesired byproducts of the production. In some embodiments, an isolated immunoglobulin herein will be purified (1) to greater than 95% by weight, or greater than 98% by weight, or greater than 99% by weight, as determined by SDS-PAGE or SEC-HPLC methods, (2) to a degree sufficient to obtain at least 15 residues of N-terminal or internal amino acid sequence by use of an amino acid sequencer, or (3) to homogeneity by SDS-PAGE under reducing or non-reducing conditions using Coomassie blue or, preferably, silver stain. Ordinarily, an isolated immunoglobulin will be prepared by at least one purification step.

The term "specific binding" or "specifically binds to" or is "specific for" refers to the binding of a binding moiety to a binding target, such as the binding of an immunoglobulin to a target antigen, e.g., an epitope on a particular polypeptide, peptide, or other target (e.g. a glycoprotein target), and means binding that is measurably different from a non-specific interaction (e.g., a non-specific interaction can be binding to bovine serum albumin or casein). Specific binding can be measured, for example, by determining binding of a binding moiety, or an immunoglobulin, to a target molecule compared to binding to a control molecule. For example, specific binding can be determined by competition with a control molecule that is similar to the target, for example, an excess of non-labeled target. In this case, specific binding is indicated if the binding of the labeled target to a probe is competitively inhibited by excess unlabeled target. The term "specific binding" or "specifically binds to" or is "specific for" a particular polypeptide or an epitope on a particular polypeptide target as used herein can be exhibited, for example, by a molecule having a $K_d$ for the target of at least about 200 nM, alternatively at least about 150 nM, alternatively at least about 100 nM, alternatively at least about 60 nM, alternatively at least about 50 nM, alternatively at least about 40 nM, alternatively at least about 30 nM, alternatively at least about 20 nM, alternatively at least about 10 nM, alternatively at least about 8 nM, alternatively at least about 6 nM, alternatively at least about 4 nM, alternatively at least about 2 nM, alternatively at least about 1 nM, or greater. In certain instances, the term "specific binding" refers to binding where a molecule binds to a particular polypeptide or epitope on a particular polypeptide without substantially binding to any other polypeptide or polypeptide epitope.

"Binding affinity" refers to the strength of the sum total of noncovalent interactions between a single binding site of a molecule (e.g., an immunoglobulin) and its binding partner (e.g., an antigen). Unless indicated otherwise, as used herein, "binding affinity" refers to intrinsic binding affinity which reflects a 1:1 interaction between members of a binding pair (e.g., immunoglobulin and antigen). The affinity of a molecule X for its partner Y can generally be represented by the dissociation constant ($K_d$). For example, the $K_d$ can be about 200 nM, 150 nM, 100 nM, 60 nM, 50 nM, 40 nM, 30 nM, 20 nM, 10 nM, 8 nM, 6 nM, 4 nM, 2 nM, 1 nM, or stronger. Affinity can be measured by common methods known in the art, including those described herein. Low-affinity antibodies generally bind antigen slowly and tend to dissociate readily, whereas high-affinity antibodies generally bind antigen faster and tend to remain bound longer. A variety of methods of measuring binding affinity are known in the art.

As used herein, the "$K_d$" or "$K_d$ value" refers to a dissociation constant measured by a technique appropriate for the immunoglobulin and target pair, for example using surface plasmon resonance assays, for example, using a Biacore X100 or a Biacore T200 (GE Healthcare, Piscataway, N.J.) at 25° C. with immobilized antigen CM5 chips.

The terms "conjugate," "conjugated," and "conjugation" refer to any and all forms of covalent or non-covalent linkage, and include, without limitation, direct genetic or chemical fusion, coupling through a linker or a cross-linking agent, and non-covalent association.

The term "fusion" is used herein to refer to the combination of amino acid sequences of different origin in one polypeptide chain by in-frame combination of their coding nucleotide sequences. The term "fusion" explicitly encompasses internal fusions, i.e., insertion of sequences of different origin within a polypeptide chain, in addition to fusion to one of its termini. The term "fusion" is used herein to refer to the combination of amino acid sequences of different origin.

The term "epitope" includes any molecular determinant capable of specific binding to an immunoglobulin. In certain aspects, epitope determinants include chemically active surface groupings of molecules such as amino acids, sugar side chains, phosphoryl, or sulfonyl, and, in certain aspects, can have specific three dimensional structural characteristics, and/or specific charge characteristics. An epitope is a region of an antigen that is bound by an immunoglobulin. A "binding region" is a region on a binding target bound by a binding molecule.

The term "target" or "binding target" is used in the broadest sense and specifically includes polypeptides, without limitation, nucleic acids, carbohydrates, lipids, cells, and other molecules with or without biological function as they exist in nature.

The term "antigen" refers to an entity or fragment thereof, which can bind to an immunoglobulin or trigger a cellular immune response. An immunogen refers to an antigen, which can elicit an immune response in an organism, particularly an animal, more particularly a mammal including a human. The term antigen includes regions known as antigenic determinants or epitopes, as defined above.

An "antigen-binding site" or "antigen-binding region" of an immunoglobulin of the present invention typically contains six complementarity determining regions (CDRs) within each variable domain, and which contribute in varying degrees to the affinity of the binding site for antigen. In each variable domain there are three heavy chain variable domain CDRs (CDRH1, CDRH2 and CDRH3) and three light chain variable domain CDRs (CDRL1, CDRL2 and CDRL3). The extent of CDR and framework regions (FRs) is determined by comparison to a compiled database of amino acid sequences in which those regions have been defined according to variability among the sequences and/or structural information from antibody/antigen complexes. Also included within the scope of the invention are functional antigen binding sites comprised of fewer CDRs (i.e., where binding specificity is determined by three, four or five CDRs). Less than a complete set of 6 CDRs can be sufficient for binding to some binding targets. Thus, in some instances, the CDRs of a $V_H$ or a $V_L$ domain alone will be sufficient. Furthermore, certain antibodies might have non-CDR-associated binding sites for an antigen. Such binding sites are specifically included within the present definition.

The term "host cell" as used in the current application denotes any kind of cellular system which can be engineered to generate the immunoglobulins according to the current invention. In one aspect, Chinese hamster ovary (CHO) cells are used as host cells. In some embodiments, *E. coli* can be used as host cells.

As used herein, the expressions "cell," "cell line," and "cell culture" are used interchangeably and all such designations include progeny. Thus, the words "transformants" and "transformed cells" include the primary subject cell and cultures derived therefrom without regard for the number of transfers. It is also understood that all progeny may not be precisely identical in DNA content, due to deliberate or inadvertent mutations. Variant progeny that have the same function or biological activity as screened for in the originally transformed cell are included.

A nucleic acid is "operably linked" when it is placed in a functional relationship with another nucleic acid sequence. For example, DNA for a pre-sequence or secretory leader is operably linked to DNA for a polypeptide if it is expressed as a pre-protein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous, and, in the case of a secretory leader, contiguous and in reading frame. However, enhancers do not have to be contiguous. Linking is accomplished by ligation at convenient restriction sites. If such sites do not exist, the synthetic oligonucleotide adaptors or linkers are used in accordance with conventional practice.

"Percent (%) amino acid sequence identity" with respect to a peptide or polypeptide sequence, i.e., the h38C2 antibody polypeptide sequences identified herein, is defined as the percentage of amino acid residues in a candidate sequence that are identical with the amino acid residues in the specific peptide or polypeptide sequence after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or Megalign (DNASTAR) software. Those skilled in the art can determine appropriate parameters for measuring alignment, including any algorithms needed to achieve maximal alignment over the full length of the sequences being compared.

"Treating" or "treatment" refers to both therapeutic treatment and prophylactic or preventative measures, wherein the object is to prevent or slow down (lessen) a targeted pathologic condition or disorder. Those in need of treatment include those already with the disorder, as well as those prone to have the disorder, or those in whom the disorder is to be prevented. For example, a subject or mammal is successfully "treated" for cancer, if, after receiving a therapeutic amount of a subject immunoconjugate according to the methods of the present invention, the subject shows observable and/or measurable reduction in or absence of one or more of the following: reduction in the number of cancer cells or absence of the cancer cells; reduction in the tumor size; inhibition (i.e., slowing to some extent and preferably stopping) of cancer cell infiltration into peripheral organs, including the spread of cancer into soft tissue and bone; inhibition (i.e., slowing to some extent and preferably stopping) of tumor metastasis; inhibition, to some extent, of tumor growth; and/or relief to some extent of one or more of the symptoms associated with the specific cancer; reduced morbidity and/or mortality, and improvement in quality of life issues.

In one aspect, the invention provides modified 38C2 catalytic antibodies which have the reactive Lys99 residue functionalized with a heteroaryl methylsulfonyl compound linker. The 38C2 catalytic antibody and its humanized variant are well known in the art and extensively characterized in the art, e.g., Wagner et al., Science 270, 1797-1800, 1995; Barbas, et al., Science 278, 2085-2092, 1997; and Rader et al., J. Mol. Biol. 332, 889-899, 2003. FIG. 1 of Rader et al., J. Mol. Biol. 332, 889-899, 2003 depicts amino acid sequences of VL and VH of mouse 38C2 (m38C2) and humanized 38C2 (h38C2). VL of m38C2 is SEQ ID NO:1, VH of m38C2 is SEQ ID NO:2, VL of h38C2 is SEQ ID NO:3, and VL of h38C2 is SEQ ID NO:4. The heavy chain variable region of the 38C2 antibody includes a single, uniquely reactive lysine residue (Lys99) that can react with a linker, thereby providing an attachment point for conjugation with a drug moiety. As such, immunoglobulin molecules that include a variable domain of the 38C2 antibody contain two such attachment points (one on each heavy chain) that can be used for conjugation with a drug moiety or other agent. Once a reactive lysine residue has been conjugated to a linker, the 38C2 antibody no longer exhibits catalytic activity. There have been a number of examples of antibody-conjugated drug compounds generated by the use of the reactive lysine residue (Lys99) in the active site of catalytic antibody 38C2 for site-specific bioconjugation. See, e.g., Rader, Proc. Natl. Acad. Sci. U.S.A 100, 5396-5400, 2003; Rader, Trends Biotechnol 32, 186-197, 2014; and U.S. Pat. No. 8,252,902. In these examples, attachment of the drug moiety to the reactive Lys99 residue of the 38C2 antibody is achieved via functionalization with a β-diketone or β-lactam based linker moiety.

By utilizing alternative irreversible covalent conjugation chemistries, the modified 38C2 antibody compounds of the invention provide alternative means for bioconjugation. Typically, the modified or linker functionalized 38C2 antibody compounds of the invention contain the 38C2 catalytic antibody that is functionalized with a heteroaryl methylsulfonyl compound. Various heteroaryl methylsulfonyl compounds can be employed in the practice of the invention. These include many methylsulfonyl 5-member monocyclic compounds, such as phenyltetrazoles or phenyloxadiazoles, that are well known in the art. See, e.g., Toda et al., Angew Chem Int Ed Engl, 52:12592-6, 2013; and Patterson et al., Bioconjug Chem, 25:1402-7, 2014. In some embodiments, the heteroaryl methylsulfonyl compound for functionalizing antibody 38C2 or derivatizing an agent moiety (e.g., a drug compound) is methylsulfone phenyloxadiazole (MS-PODA) as exemplified herein.

In a related aspect, the invention provides antibody-agent conjugates that contain at least one agent that is site-specifically conjugated to catalytic antibody 38C2 via a heteroaryl methylsulfonyl compound linker. These antibody agent conjugates include, e.g., antibody conjugated drugs (ADCs) such as antibody conjugated small molecule drugs and antibody conjugated nucleic acid (e.g., siRNA) drugs, dual variable domain (DVD) antibody-conjugated drugs, chemically programmed antibodies, bispecific antibodies, and chimeric antigen receptors. In another related aspect, the invention provides pharmaceutical compositions that contain an effective amount of an antibody-agent conjugate of the invention and optionally a pharmaceutically acceptable carrier. In another related aspect, the invention provides methods for producing the antibody-agent conjugates described herein. In some embodiments, the antibody-agent conjugates of the invention are generated by first functionalizing the 38C2 antibody with a heteroaryl methylsulfonyl compound described above, followed by reacting the functionalized antibody with the agent moiety (a drug moiety or a targeting moiety and etc.). In some other embodiments, the agent moiety can be first derivatized with the heteroaryl methylsulfonyl compound as exemplified herein, and followed by reacting the derivatized agent moiety with the antibody. In some preferred embodiments, the methylsulfonyl compound for derivatizing an agent moiety is MS-PODA.

The linker functionalized 38C2 antibodies and antibody-agent conjugates of the invention can be readily produced via routinely practiced methods, e.g., recombinant expression as exemplified herein. Functionalizing a 38C2 antibody (e.g., h38C2) with a heteroaryl methylsulfonyl compound can be readily performed in accordance with known chemistry techniques or the protocols exemplified herein. See, e.g., Example 5 and FIGS. 1-2 herein. Similarly, derivatizing an agent moiety with a methylsulfonyl compound and conjugating the derivatized agent moiety to the 38C2 antibody can be readily carried out in accordance with the protocols exemplified herein (see, Example 5). For example, derivatizing a drug moiety for generating antibody-drug conjugates of the invention can be performed using the methods exemplified herein for MS-PODA derivatized MMAF. Similarly, derivatizing a targeting moiety for generating chemically programmed antibodies of the invention can be performed using methods exemplified herein for MS-PODA derivatized folate or LLP2A. Methods for derivatizing a hapten or drug moiety with a methylsulfonyl compound are also described in the art. See, e.g., Toda et al., Angew Chem Int Ed Engl, 52:12592-6, 2013.

Once the agent moiety (e.g., a drug moiety or a targeting moiety) is derivatized with a methylsulfonyl compound, antibody-agent conjugates (e.g., ADCs) of the invention can be readily assembled in accordance with methods known in the art or the specific protocols exemplified herein. See, e.g., Example 5 and FIG. 6 herein; Rader, Trends Biotechnol 32, 186-197, 2014; Toda et al., Angew Chem Int Ed Engl, 52:12592-6, 2013; and Patterson et al., Bioconjug Chem, 25:1402-7, 2014. Typically, as exemplified herein with h38C2-fluorescein conjugate and h38C2-MMAF conjugate, the derivatized agent is provided in molar excess when reacting with the 38C2 antibody. DVD-Ig antibody compounds can also be produced in accordance with the protocols exemplified herein and methods that have been described in the art. See, e.g., Nanna et al., Nat. Commun. 8:1112, 2017; and WO2017/049139.

In the linker functionalized 38C2 antibody compounds or antibody-agent conjugates of the invention, the Lys99 residue in either one or both antibody arms can be functionalized with the heteroaryl methylsulfonyl compound. Thus, in some embodiments, the 38C2 antibody in the antibody compounds or antibody-agent conjugates is a homodimeric molecule that contains the Lys99 residue that is functionalized with the heteroaryl methylsulfonyl compound in both antibody arms. In some of these embodiments, the antibody-agent conjugates (e.g., ADCs) can contain the same agent moiety (e.g., a drug moiety) that is conjugated to the reactive Lys residue via a heteroaryl methylsulfonyl compound linker. In some embodiments, the 38C2 antibody in the antibody compounds or antibody-agent conjugates is a heterodimeric molecule that is functionalized with or contains the heteroaryl methylsulfonyl compound linker in just one antibody arm. Heavy chain heterodimerization for such molecules can be accomplished, e.g., via knobs-into-holes mutations. In some of these embodiments, the antibody-agent conjugates can contain a first agent (e.g., a drug moiety) that is conjugated to one antibody arm via the heteroaryl methylsulfonyl compound linker and a second agent (e.g., a different drug moiety) that is conjugated to the other antibody arm via a diketone or β-lactam based linker.

Either a full length 38C2 antibody (e.g., IgG1) or antibody fragment thereof can be employed in the practice of the invention. Suitable antibody fragments (or "antigen-binding fragments") derived from 38C2 include, e.g., Fab, Fab', F(ab')₂, Fv or scFv. In some preferred embodiments of the linker modified or functionalized 38C2 antibody compounds or the antibody-agent conjugates of the invention, the employed antibody is a humanized 38C2 antibody (h38C2) or antigen-binding fragment thereof alone. Some antibody-agent conjugates of the invention are dual variable domain (DVD) compounds (e.g., DVD-Fab or DVD-Ig) or bispecific antibodies that harbors a 38C2 functionalized or derivatized with a heteroaryl methylsulfonyl compound. In some of these embodiments, the DVD-Ig contains a first variable domain that binds to a target antigen (e.g., a tumor cell surface antigen or receptor such as HER2 as exemplified herein) and a second variable domain (38C2) that is conjugated to a drug moiety via a heteroaryl methylsulfonyl compound linker.

The antibody-agent conjugates of the invention can be used for delivering various agents or payloads (e.g., a drug) to the specific target of interest. The payload broadly includes, but are not limited to, biologically active moieties, such as drug moieties and expression modifying moieties, as well as non-biologically active moieties, such as detectable moieties (e.g., detectable labels). Non-limiting examples of drug moieties include cytotoxic and cytostatic agents that are capable of killing a target cell, or arresting the growth of a target cell. In some embodiments, the employed drug moieties are toxins, chemotherapeutic agents, antibiotics, radioactive isotopes, chelated radioactive isotopes, and nucleolytic enzymes. In some embodiments, the drug moieties for the ADCs of the invention can be polymerized drugs that consist of a polymer drugs. For example, the payload in the ADCs can be polymerized drugs generated via the Fleximer technology developed by Mersana Therapeutics (Cambridge, MA). See, e.g., Yurkovetskiy et al., Cancer Res. 2015, 75:3365-72.

In various embodiments, the payload in the ADCs of the invention is a drug moiety selected from the group consisting of auristatin; dolostatin; cemadotin; amanitin (including but not limited to α-amanitin); monomethyl auristatin F (MMAF); Monomethyl auristatin E (MMAE); maytansinoids (including, but not limited to DM1, DM3 and DM4); pyrrolobenzodiazepines (PBDs, including, but not limited to monomeric and dimeric PBDs); indolinobenzodiazepine (including, but not limited to dimeric indolinobenzodiazepines); enediynes (including but not limited to calicheamicins and tiancimycins); camptothecins (including but not limited to SN-38); doxorubicin (including but not limited to MMDX or bioactivation products thereof, such as, e.g., PNU-159682); a duocarmycine. In some embodiments, the drug moiety in the ADCs of the invention is selected from a group consisting of a V-ATPase inhibitor, a pro-apoptotic agent, a Bcl2 inhibitor, an MCL1 inhibitor, a HSP90 inhibitor, an IAP inhibitor, an mTor inhibitor, a microtubule stabilizer, a microtubule destabilizer, an auristatin, a dolastatin, a maytansinoid, a MetAP (methionine aminopeptidase), an inhibitor of nuclear export of proteins CRM1, a DPPIV inhibitor, a proteasome inhibitor, an inhibitor of phosphoryl transfer reactions in mitochondria, a protein synthesis inhibitor, a kinase inhibitor, a CDK2 inhibitor, a CDK9 inhibitor, a kinesin inhibitor, an HDAC inhibitor, a DNA damaging agent, a DNA alkylating agent, a DNA intercalator, a DNA minor groove binder and a DHFR inhibitor.

In some embodiments, the antibody-agent conjugates of the invention are ADCs that contain a drug moiety that modifies a given biological response. Drug moieties are not to be construed as limited to classical chemical therapeutic agents. For example, a drug moiety can be a protein, peptide, or polypeptide possessing a desired biological activity. Such proteins can include, for example, a toxin such as abrin, ricin A, pseudomonas exotoxin, cholera toxin, or diphtheria toxin, a protein such as tumor necrosis factor, α-interferon, β-interferon, nerve growth factor, platelet derived growth factor, tissue plasminogen activator, a cytokine, an apoptotic agent, an anti-angiogenic agent, or a biological response modifier such as, for example, a lymphokine. In some embodiments, the drug moiety can be a cytotoxin, a drug (e.g., an immunosuppressant) or a radiotoxin. Examples of cytotoxins include but are not limited to, taxanes, DNA-alkylating agents (e.g., CC-1065 analogs), anthracyclines, tubulysin analogs, duocarmycin analogs, auristatin E, auristatin F, maytansinoids, and cytotoxic agents comprising a reactive polyethylene glycol moiety, taxon, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof.

Drug moieties can also include, for example, anti-metabolites (e.g., methotrexate, 6-mercaptopurine, 6-thioguanine, cytarabine, 5-fluorouracil decarbazine), ablating agents (e.g., mechlorethamine, thiotepa chlorambucil, meiphalan, carmustine (BSNU) and lomustine (CCNU), cyclophosphamide, busulfan, dibromomannitol, streptozotocin, mitomycin C, and cis-dichlorodiamine platinum (II) (DDP) cisplatin, anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine and vinblastine). See, e.g., US Patent Publication No. 20090304721, which is incorporated herein by reference in its entirety. Other non-limiting examples of cytotoxins that can be conjugated to the antibodies, antibody fragments (antigen binding fragments) or functional equivalents of the invention include duocarmycins, calicheamicins, maytansines and auristatins, and derivatives thereof.

The payloads in the antibody-agent conjugates of the invention can also be a radioactive isotope or a chelated radioactive isotope to generate cytotoxic radiopharmaceuticals, referred to as radioimmunoconjugates. Examples of radioactive isotopes that can be conjugated to antibodies for use diagnostically or therapeutically include, but are not limited to, iodine-131, indium-111, yttrium-90, lutetium-177, bismuth-213 and astatine-211. Methods for preparing radioimmunoconjugates are established in the art. Examples of radioimmunoconjugates are commercially available, including Zevalin™ (DEC Pharmaceuticals) and Bexxar™ (Corixa Pharmaceuticals), and similar methods can be used to prepare radioimmunoconjugates using the antibodies of the invention. In some embodiments, the macrocyclic chelator is 1,4,7,10-tetraazacyclododecane-N,N',N'',N'''-tetraacetic acid (DOTA) which can be attached to an immunoglobulin via a linker molecule.

In some embodiments, the payload of the antibody-agent conjugates of the invention can be a photoabsorber for near infrared (NIR) photoimmunotherapy (PIT). PIT is a new tumor-targeted anticancer platform that can induce a rapid and specific destruction of the tumor. The treatments consist of a drug (a cancer-targeting photoactivatable antibody conjugate) and a device system to apply light at the tumor site. PIT is unique in that it combines molecular targeting of the cancer cells to achieve high tumor specificity, together with a biophysical mechanism of cancer cell destruction that results in broad spectrum anticancer activity regardless of the tumorigenic mechanism of the patients' tumor. See, e.g., Mitsunaga et al., Nat. Med. 17:1685-92, 2011. For example, the DVD compounds of the invention can include a NIR PIT photoabsorber (e.g., IR700) and an antigen-binding variable domain region targeting tumor cells.

In various embodiments, the payload of the antibody-agent conjugates of the invention can be a single drug unit or a plurality of identical drug units, such as 2, 3, 4, 5, 6, 7, 8, 9, or 10 drug units on the same drug moiety. In some embodiments, the drug moiety includes two different drug units on the same drug moiety. For example, in some aspects, a single drug moiety can include both an MMAF drug unit and a PBD monomer drug unit. Furthermore, in certain aspects, a subject immunoconjugate can include a first drug moiety conjugated to a first arm of the immunoconjugate, and a second drug moiety conjugated to the second arm of the immunoconjugate. As such, any of a variety of combinations of drug moieties can be conjugated to a subject DVD-Ig via a linker.

In some embodiments, the agent moieties in the antibody-agent conjugates of the invention are expression modifying moieties. Expression modifying moieties include, but are not limited to, non-protein-coding RNA ("npcRNA"). In some embodiments, the npcRNA can be, e.g., a microRNA (miRNA), a miRNA precursor, a small interfering RNA (siRNA), a small RNA and precursor encoding same, a heterochromatic siRNA (hc-siRNA), a Piwi-interacting RNA (piRNA), a hairpin double strand RNA (hairpin dsRNA), a trans-acting siRNA (ta-siRNA), a naturally occurring antisense siRNA (nat-siRNA), a tracer RNA (tcRNA), a guide RNA (gRNA), and a single-guide RNA (sgRNA).

In some embodiments, the agent moieties in the antibody-agent conjugates of the invention are detectable moieties. Detectable moieties include, but are not limited to, labels or moieties that are detected directly (such as fluorescent, chromophoric, electron-dense, chemiluminescent, and radioactive labels), as well as moieties, such as enzymes or ligands, that are detected indirectly, e.g., through an enzymatic reaction or molecular interaction. Exemplary labels include, but are not limited to, the radioisotopes $^{32}$P, $^{14}$C, $^{125}$I, $^{3}$H, and $^{131}$I, fluorophores such as rare earth chelates or fluorescein and its derivatives, rhodamine and its derivatives including carboxytetramethylrhodamine (TAMRA), dansyl, umbelliferone, luciferases, e.g., firefly luciferase and bacterial luciferase (U.S. Pat. No. 4,737,456), luciferin, 2,3-dihydrophthalazinediones, horseradish peroxidase (HRP), alkaline phosphatase, β-galactosidase, glucoamylase, lysozyme, saccharide oxidases, e.g., glucose oxidase, galactose oxidase, and glucose-6-phosphate dehydrogenase, heterocyclic oxidases such as uricase and xanthine oxidase, coupled with an enzyme that employs hydrogen peroxide to oxidize a dye precursor such as HRP, lactoperoxidase, or microperoxidase, biotin/avidin, spin labels, bacteriophage labels, stable free radicals, and the like.

In another aspect, the invention provides methods of using the antibody-agent conjugates (e.g., DVD-ADCs) described herein in various therapeutic or diagnostic applications. The specific application of an antibody-agent conjugate of the invention will depend on the payload or drug moiety conjugated to the antibody compound. When a DVD based ADC is used, the specific application is also depending on the target molecule that is recognized by the second variable domain in the DVD. Thus, the antibody-agent conjugates described herein can be readily applied in many specific cancer therapies. Such therapeutic applications include, e.g., delivery of drug moieties to tumors via a known tumor targeting antibody or antigen-binding variable domain as exemplified herein. They also include treatments not directly targeting tumor cells, e.g., antibody-siRNA conjugates for targeting T cells, other immune cells, and tumor-supporting cells. They further include other non-conventional cancer therapies, e.g., the use of near infrared (NIR) photoimmunotherapy (PIT) for treating tumors (as well as non-tumor cells). In some embodiments, the invention provides methods that employ DVD-ADC compounds that target tumor cells expressing a particular tumor antigen, e.g., HER2 as exemplified herein. Suitable types of cancers include, without limitation, hematologic cancers, carcinomas, sarcomas, melanoma, and central nervous system cancers. In some other embodiments, the compounds of the invention (e.g., DVD based ADCs) can also be used in treating non-oncology indications such as infectious diseases, autoimmune diseases, cardiovascular diseases, metabolic diseases. See, e.g., Beck et al., Nat Rev Drug Discov. 2017, 16:315-337.

EXAMPLES

The following examples are offered to illustrate, but not to limit the present invention.

Example 1 in Silico Arylation of Lys99

The nucleophilicity of the ε-amino group of Lys99 of h38C2 prompted us to investigate alternative irreversible covalent conjugation chemistries that could further increase the accessible payload space. Due to the hydrophobicity of the Lys99 microenvironment, we hypothesized that Lys arylation, which has not been reported for antibody conjugation, could provide a suitable route. Specifically, we were interested in testing heteroaryl methylsulfonyl compounds as serum-stable alternative to maleimide-based conjugation to antibodies with engineered free Cys residues. Our studies focused on the methylsulfone phenyloxadiazole (MS-PODA) (FIG. 1A).

Figure 1B:
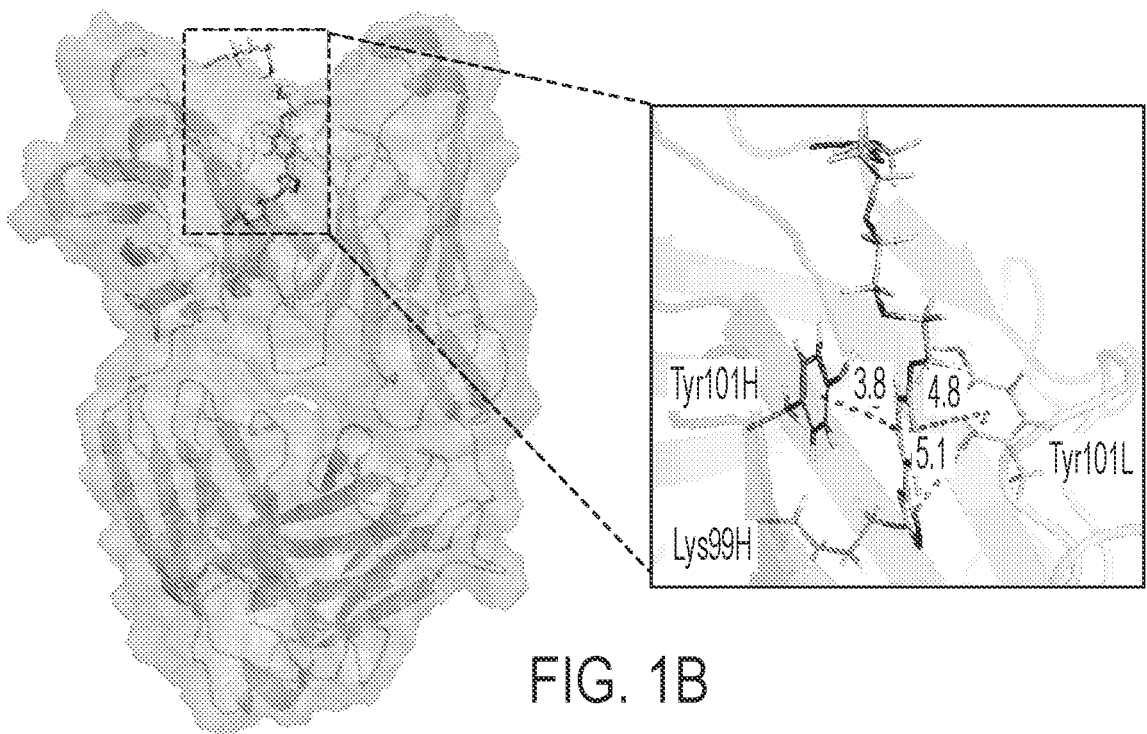
Figure 7:
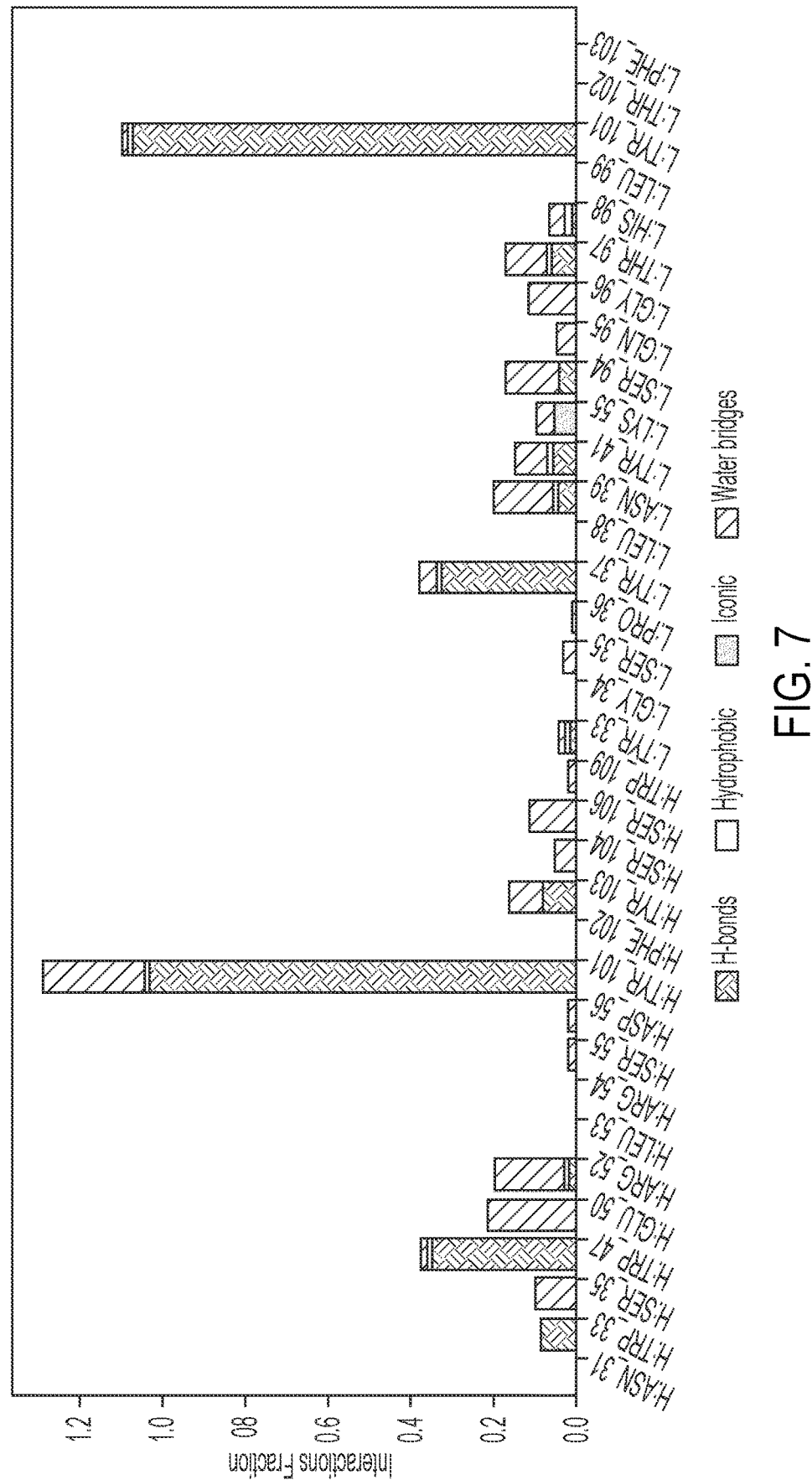
FIG. 7. Small molecule-antibody interactions in the in silico docking model of PODA-conjugated Lys99. Starting with the crystal structure of h38C2_Arg Fab (PDB ID 6U85), Arg99 was replaced with an azido-(PEG)$_4$-PODA-derivatized Lys residue and subjected to energy minimization in silico. Small molecule-antibody interactions were categorized into the four types shown and displayed as stacked bar chart for each interacting $V_H$ or $V_L$ residue. The stacked bar charts are normalized over the course of the trajectory with a value of 1.0 suggesting that 100% of the simulation time the specific interaction is maintained. Tyr101 of $V_H$ and Tyr 101 of $V_L$ have values over 1.0 due to their multiple contacts.

Based on the proposed reaction of MS-PODA with the ε-amino group of Lys99 (FIG. 1A), we used computational modeling to dock the compound into the hydrophobic pocket of h38C2. This was based on the recently solved crystal structure of h38C2 Fab with a Lys99Arg mutation (PDB ID 6U85). Arg99 was replaced with an azido-(PEG)$_4$-PODA-derivatized Lys residue and subjected to energy minimization in silico. Residues in the hydrophobic pocket interacting with PODA were identified and their interatomic distances were calculated (FIG. 1B). Two tyrosine (Tyr) residues, Tyr101 of $V_H$ and Tyr101 of the variable light chain domain ($V_L$) dominated the interactions through π-π stacking with the phenyl ring of PODA (FIG. 7). Tyr101 of $V_L$ and a tryptophan (Trp) residue, Trp47 of $V_H$, revealed a π-π stacking interaction with oxadiazole ring of PODA. Several hydrogen bonds bridged by water molecules also contributed to the interaction (FIG. 7). Collectively, computational modeling suggested that MS-PODA can serve as hapten-like compound for covalent conjugation to Lys99.

Example 2 Arylation of Lys99 Probed with MS-PODA Derivative of Fluorescein

Figures 2A, 2B:
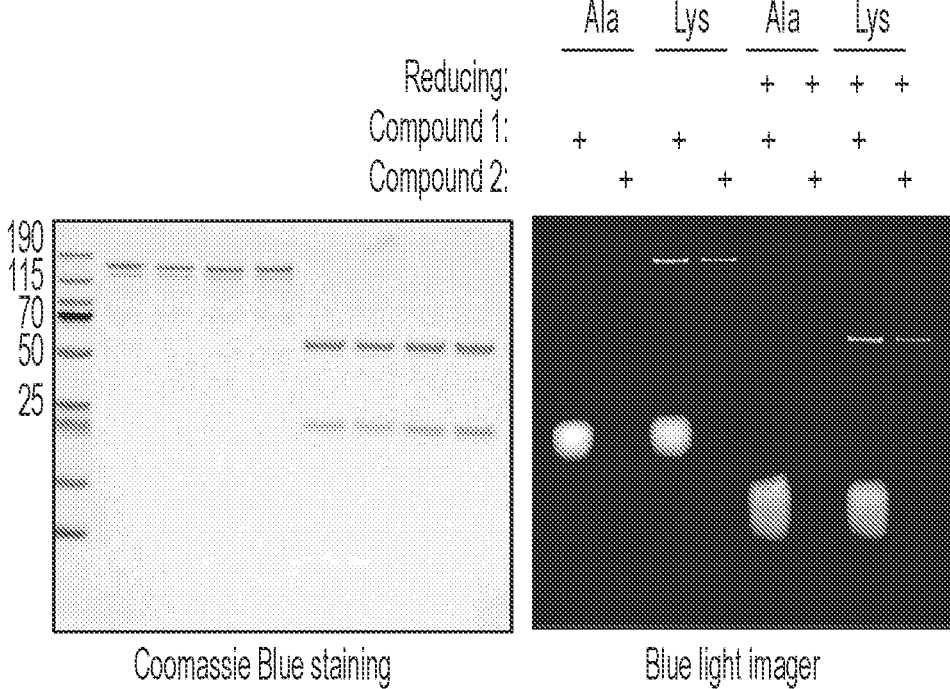
FIG. 2. Site-specific conjugation of MS-PODA to Lys99 of h38C2. (A) Structures of the MS-PODA derivative of fluorescein (compound 1) and the β-lactam hapten derivative of TAMRA (compound 2) used in this study. (B) Unpurified fluorescein- and TAMRA-conjugated (5 equiv) h38C2 ("Lys") and h38C2_Lys99Ala ("Ala") IgG1 were separated by SDS-PAGE under nonreducing or reducing conditions and analyzed by Coomassie Blue staining and in-gel fluorescence. (C) MALDI-TOF analysis of the reduced and deglycosylated (PNGase F) unconjugated (left) and compound 1-conjugated (right) h38C2 IgG1. The expected masses for the unconjugated heavy and light chains were 49 460 and 23 955 Da, respectively. The expected mass for the heavy chain with one conjugated compound 1 was 50 055 Da. The peak at 34 781 Da corresponds to PNGase F. (D) Catalytic activity of h38C2 IgG1 before and after conjugation to compound 1. Unconjugated (●) and conjugated (■) antibody (1 μM) was measured using the retro-aldol conversion of methodol to a detectable fluorescent aldehyde (relative fluorescent units (RFU)) and acetone. Conjugated h38C2 IgG1 completely lost catalytic activity, revealing quantitative conjugation at the two reactive Lys residues. Mean±standard deviation (SD) values of triplicates were plotted.
Figure 2C:
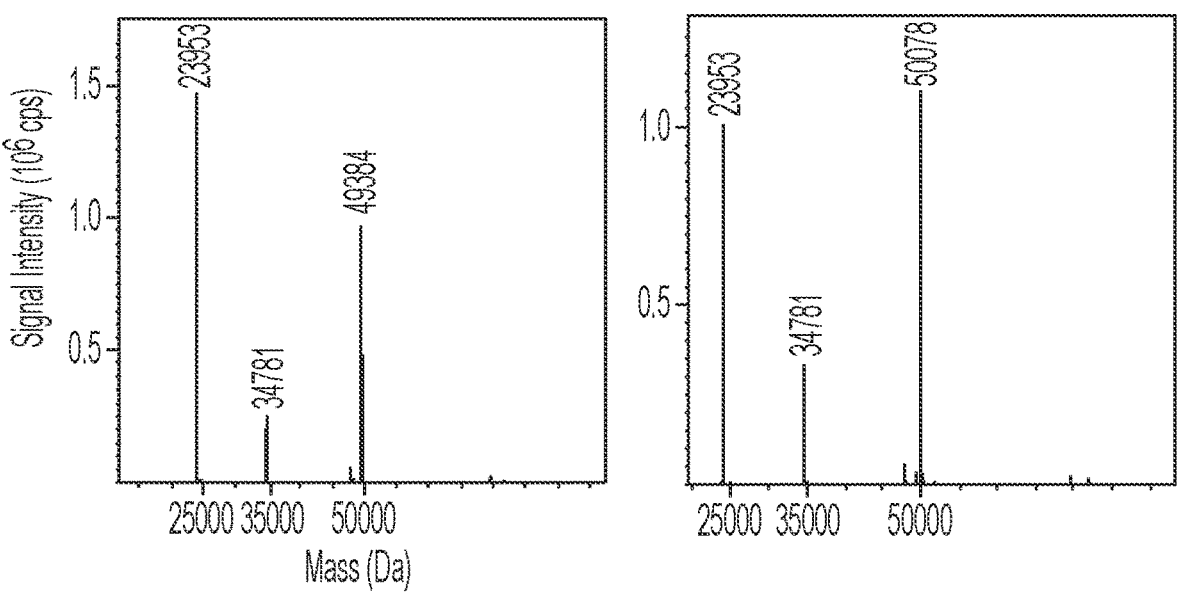
Figure 2D:
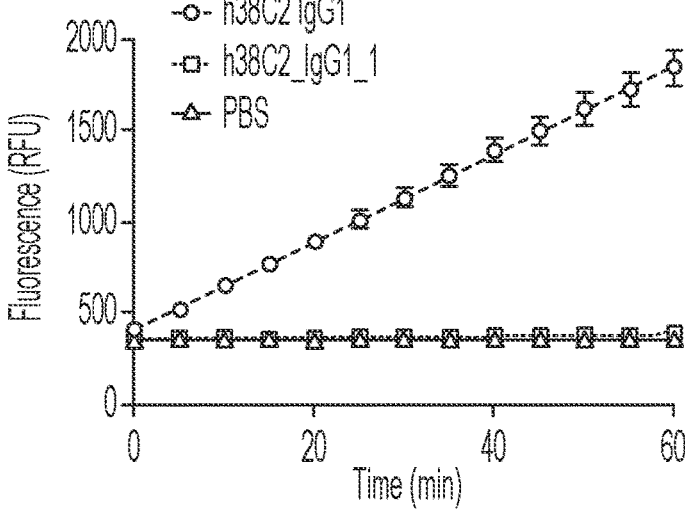

This Example describes probing of efficient, selective, and stable arylation of Lys99 with an MS-PODA derivative of fluorescein. To probe covalent conjugation to Lys99 in vitro, we used a previously described MS-PODA derivative of fluorescein (compound 1; FIG. 2A). For comparison, we included a previously described β-lactam hapten derivative of tetramethylrhodamine (TAMRA) (compound 2; FIG. 2A). To pinpoint conjugation at Lys99, we also cloned, expressed, and purified h38C2 IgG1 having a Lys99Ala mutation. Following incubation of h38C2 and h38C2_Lys99Ala IgG1 with 5-fold molar excess (5 eq per reactive Lys residue) of compounds 1 and 2 for 4 h at room temperature in PBS, unpurified antibody conjugates along with unconjugated antibody were separated by reducing and nonreducing SDS-PAGE and analyzed by Coomassie Blue staining and in-gel fluorescence (FIG. 2B). This analysis revealed conjugation of both compounds to the 50-kDa heavy chain of h38C2 IgG1 but not to the 25-kDa light chain. No conjugation to h38C2_Lys99Ala was detectable, suggesting site-specific conjugation to the reactive Lys99 residue (FIG. 2B). Mass spectrometry analysis of the PNGase F-treated (to remove N-glycosylation) and dithio-threitol (DTT)-treated (to reduce interchain disulfide bridges) unconjugated antibody revealed molecular weights of 49,384 Da (heavy chain; expected molecular weight without posttranslational modifications: 49,460 Da) and 23,953 Da (light chain; 23,955 Da) (FIG. 2C). The correspondingly prepared antibody conjugate from the reaction of h38C2 IgG1 with compound 1 revealed an increase of the molecular weight of the heavy chain by 694 Da, indicating the covalent conjugation of one PODA-fluorescein molecule. The conjugation appeared to be highly efficient and selective as only ~5% unconjugated heavy chain, no conjugated light chain, and no multiple conjugated heavy chain were detectable (FIG. 2C). Selective conjugation to the two hapten binding sites of h38C2 IgG1 was further shown by complete loss of catalytic activity mediated by Lys99 (FIG. 2D).

Figure 3:
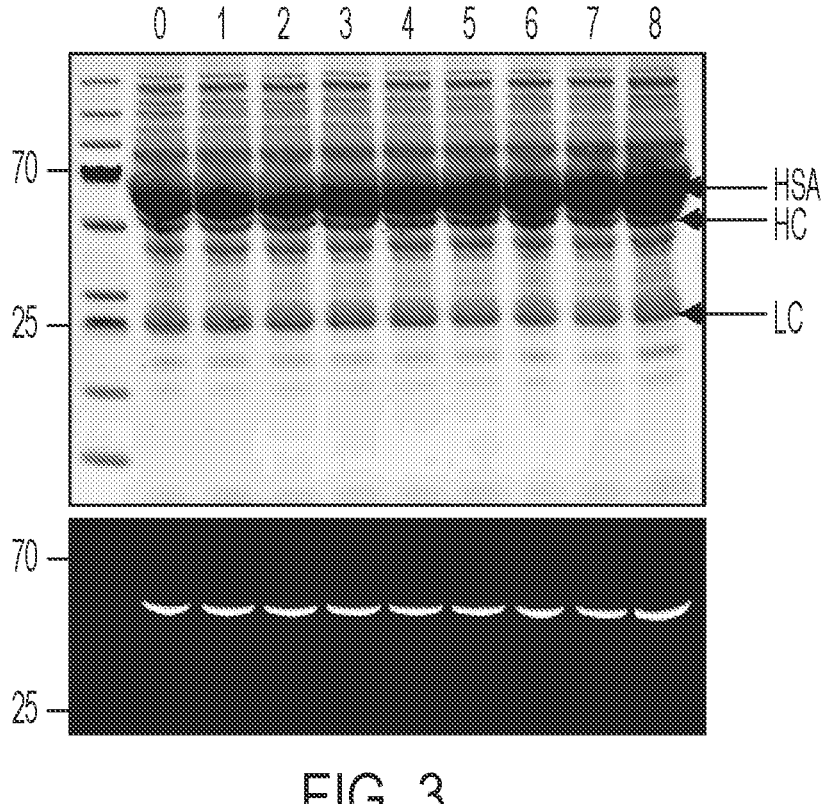
FIG. 3. Human plasma stability of the conjugate of h38C2 IgG1 and the MS-PODA derivative of fluorescein. h38C2 IgG1 was conjugated to compound 1, incubated with human plasma at 37° C., and analyzed after 0, 1, 2, 3, 4, 5, 6, 7, and 8 d by reducing SDS-PAGE followed by Coomassie Blue staining (top) and in-gel fluorescence (bottom). HSA, human serum albumin; HC, heavy chain; LC, light chain.

Next, we examined the stability of the Lys99:PODA adduct by incubating the antibody conjugate with human plasma for up to 8 days at 37° C. Analysis by reducing SDS-PAGE followed by Coomassie Blue staining and in-gel fluorescence revealed high stability of the adduct without any detectable transfer of fluorescence to plasma proteins (FIG. 3).

Example 3 MS-PODA-Mediated Chemical Programming

Figure 4A:
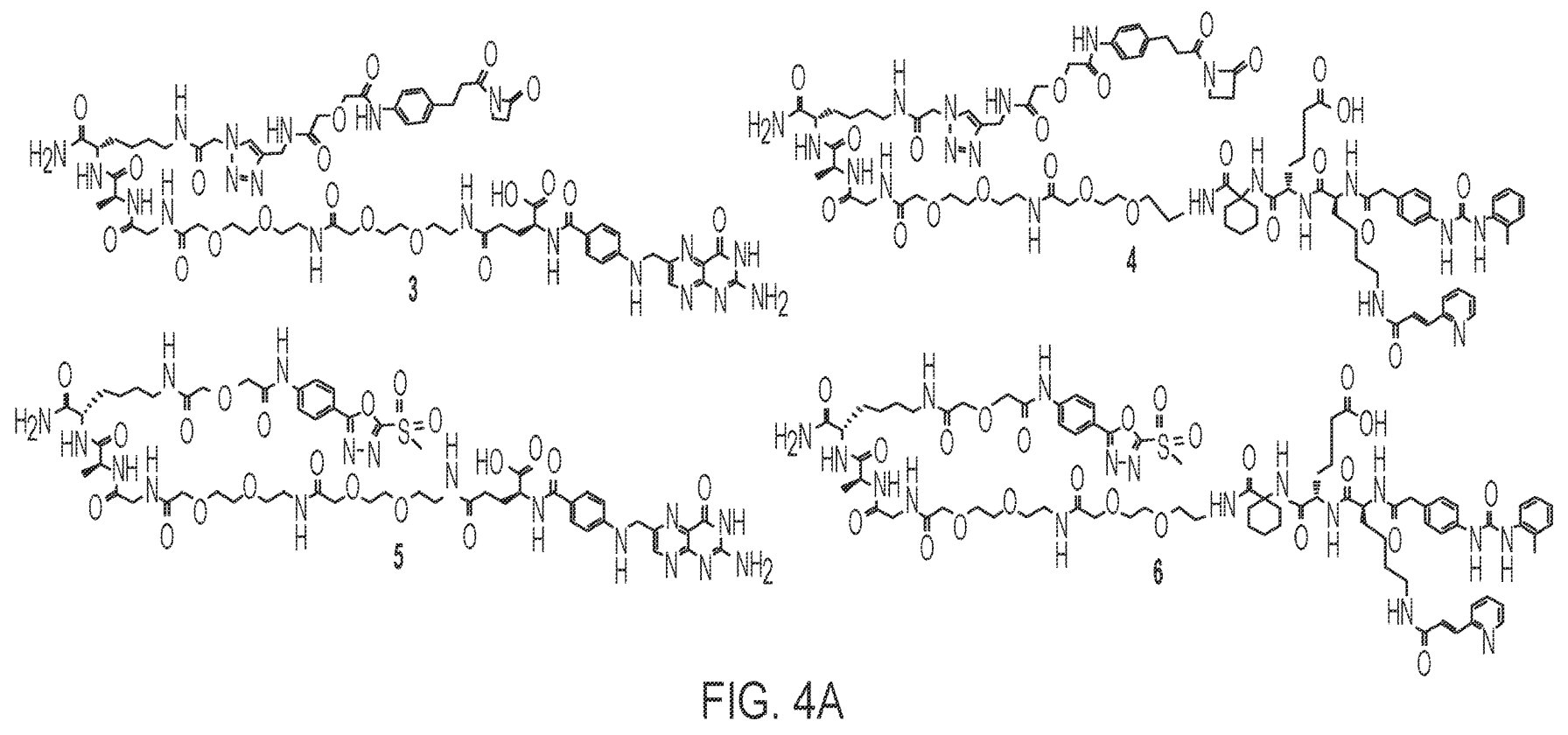

The efficient, selective, and stable conjugation of a fluorescein derivative of MS-PODA to Lys99 of h38C2 prompted us to investigate MS-PODA conjugation in the context of known therapeutic utilities of h38C2, including chemical programming.[8] To endow h38C2 with high specificity and affinity for small molecule binding sites of two different cell surface receptors, we synthesized β-lactam hapten and MS-PODA derivatives of folate (compounds 3 and 5, respectively; FIG. 4A) and LLP2A (compounds 4 and 6; respectively; FIG. 4A). It is of note that compared to β-lactam-functionalized ligands, synthetic access to MS-PODA-containing constructs is more straight forward. Preparation of MS-PODA moieties can be achieved with readily available commercial reagents and incorporation into ligands can be performed directly on solid-phase resins without intermediate purification. In contrast, synthesis of β-lactam-functionalized ligands typically involves azide-alkyne click reactions that necessitate purification of the reaction products. Folate (vitamin B9), binds with nanomolar affinity to the folate receptor 1 (FOLR1 or folate receptor a), which is overexpressed in ovarian, lung, and other cancers. LLP2A is a picomolar-affinity ligand for the open conformation of integrin $\alpha_4\beta_1$ that Lam and colleagues identified by screening a one-bead-one-compound combinatorial peptidomimetic library. The open conformation of integrin $\alpha_4\beta_1$ (activated integrin $\alpha_4\beta_1$) is found at elevated levels on malignant B cells and in other hematologic and solid malignancies, where it is involved in trafficking and metastasis. Thus, both FOLR1 and integrin $\alpha_4\beta_1$ have emerged as attractive targets for cancer therapeutics.

Figure 5B:
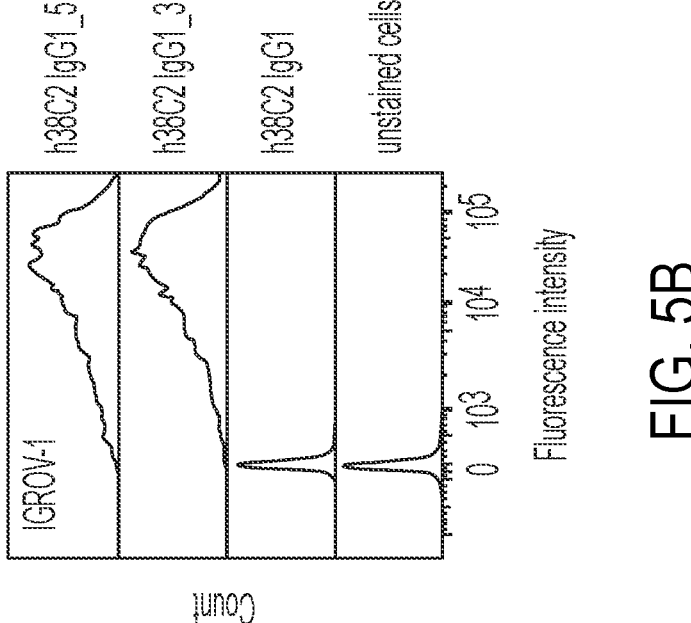
FIG. 5. Binding studies with chemically programmed h38C2 IgG1. (A) ELISA of folate-conjugated h38C2 IgG1 via β-lactam hapten (compound 3) or MS-PODA (compound 5). Recombinant human FOLR1 in TBS was used for coating, 3% (v/v) skim milk in TBS for blocking, and HRP-conjugated goat anti-human Fcγ-specific fragment pAbs for detection. Unconjugated h38C2 IgG1 served as negative control (mean±SD of triplicates). (B) Flow cytometry analysis of the same antibody conjugates and negative control using FOLR1-positive human IGROV-1 cells and FITC-conjugated goat anti-human IgG-specific pAbs for staining. (C) ELISA of LLP2A-conjugated h38C2 IgG1 via β-lactam hapten (compound 4) or MS-PODA (compound 6). Recombinant human integrin $\alpha_4\beta_1$ in TBS supplemented with 1 mM MnCl$_2$ was used for coating (mean±SD of triplicates), and the ELISA was performed as described in (A). (D) Flow cytometry analysis of the same antibody conjugates and negative control using integrin $\alpha_4\beta_1$-positive human Jurkat cells in the presence of 1 mM MnCl$_2$. The cells were stained as in (B).
Figure 5A:
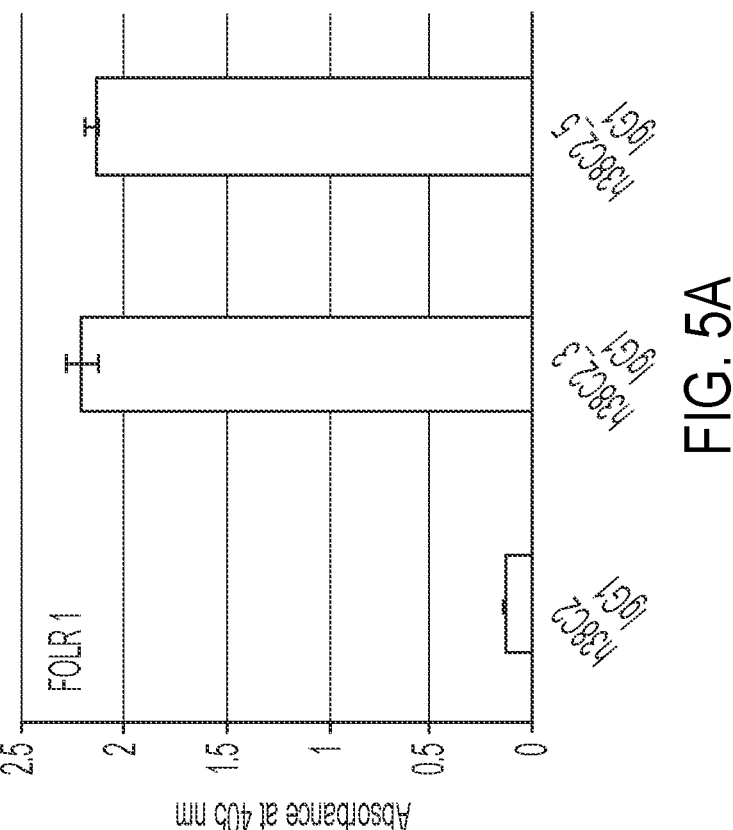
Figure 5D:
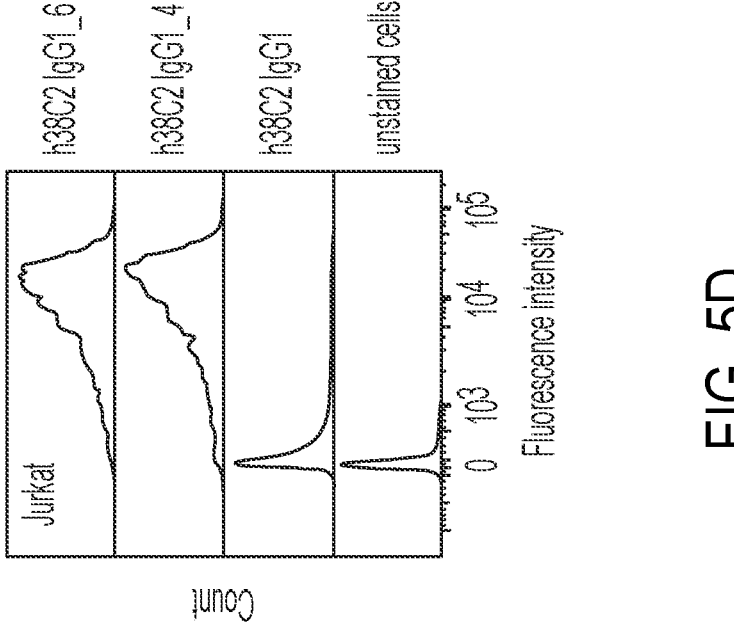
Figure 5C:
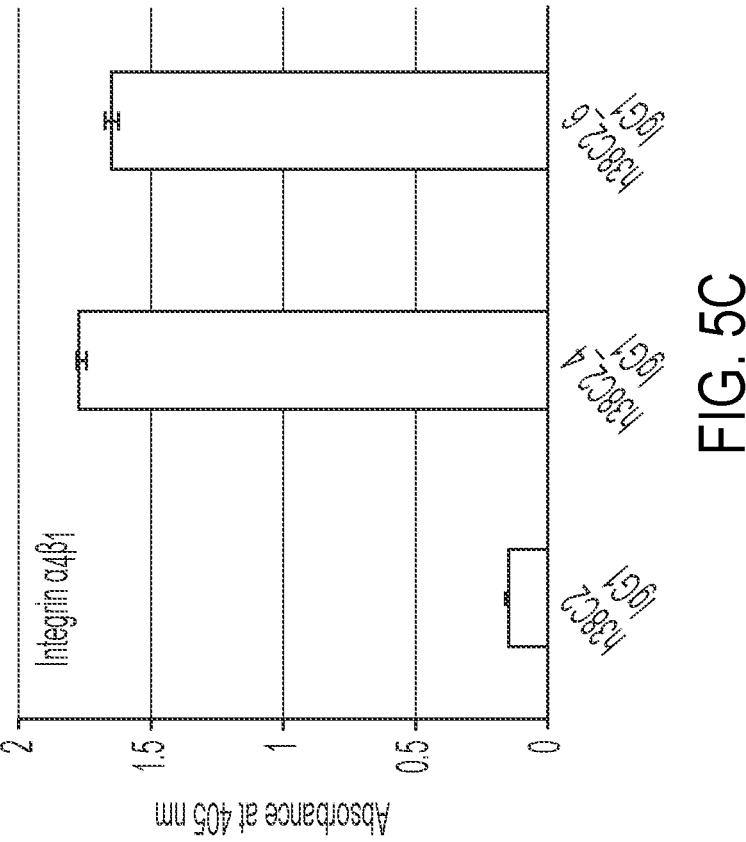

Following incubation of h38C2 IgG1 with 5-fold molar excess of compounds 3-6 for 4 h at room temperature in PBS and removal of unconjugated compound, complete loss of catalytic activity for all incubation mixtures confirmed the equivalent efficiency of β-lactam hapten and MS-PODA-mediated conjugation (FIG. 4B). At 1-fold and 2-fold molar excess (1 and 2 eq, respectively), no significant difference in the partial loss of catalytic activity was detectable between the two electrophiles (FIG. 4B). With the loss of its catalytic activity, h38C2 gained the ability to bind FOLR1 and integrin $\alpha_4\beta_1$ when chemically programmed with the folate and LLP2A derivatives, respectively. This was first shown by ELISA using recombinant FOLR1 and $Mn^{2+}$-activated integrin $\alpha_4\beta_1$ for plate coating and horseradish peroxidase (HRP)-conjugated goat anti-human Fcγ polyclonal antibodies (pAbs) for detection (FIGS. 5A and C). Subsequent flow cytometry analyses with the FOLR1-positive human ovarian cancer cell line IGROV-1 (FIG. 5B) and the $Mn^{2+}$-activated integrin $\alpha_4\beta_1$-displaying human T-cell line Jurkat (FIG. 5D) confirmed the chemical programming. No difference between the established β-lactam hapten- and the new MS-PODA-mediated chemical programming was detectable. This demonstrated that arylation of its reactive Lys residue is suitable for chemical programming of h38C2.

Example 4 MS-PODA-Mediated Assembly of Antibody-Drug Conjugates

Figure 6A:
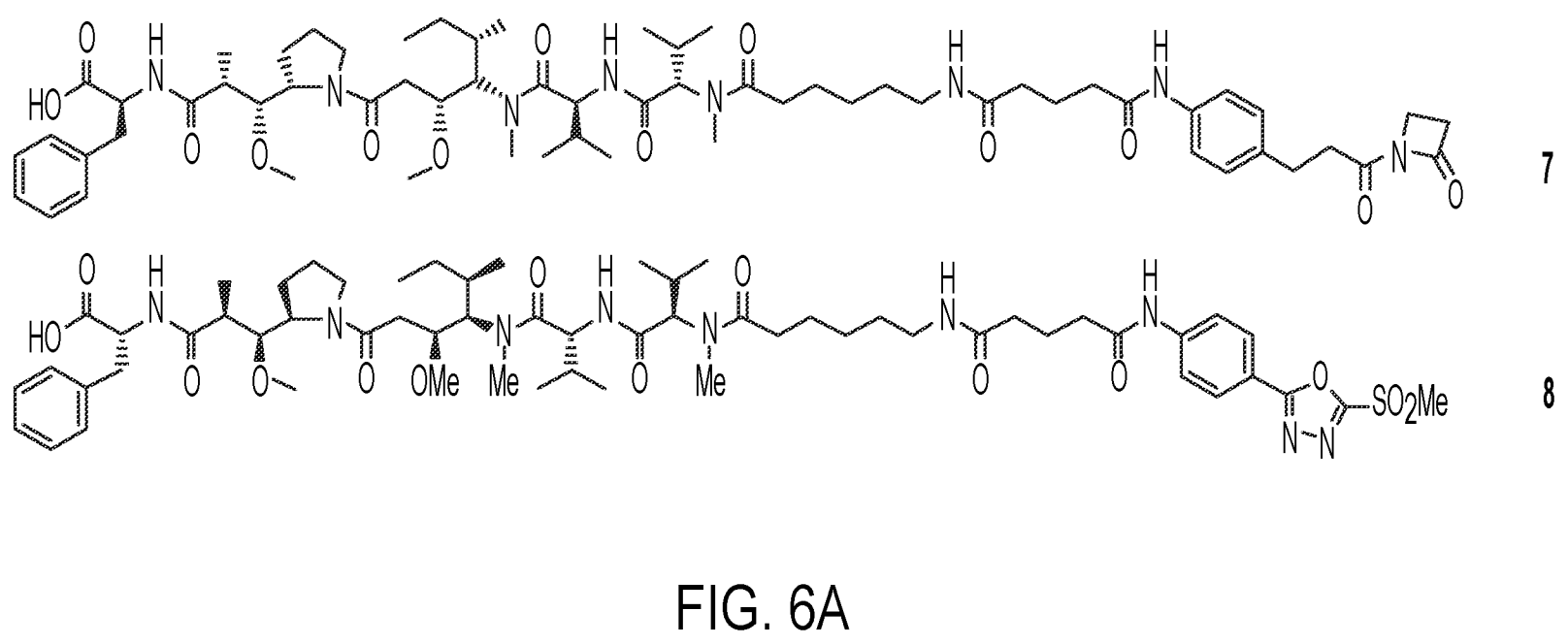

Next, we investigated MS-PODA-mediated conjugation for assembling DVD-ADCs that consist of an outer trastuzumab-based Fv that targets HER2 on breast cancer cells and an inner h38C2-based Fv that facilitates site-specific conjugation of highly cytotoxic drugs. This concept has been established for a β-lactam hapten derivative of the tubulin polymerization inhibitor monomethyl auristatin F (MMAF), shown as compound 7 in FIG. 6A. We previously reported a corresponding MS-PODA derivative of MMAF (compound 8; FIG. 6A) for site-specific conjugation to antibodies with engineered Cys residues.

Figure 6B:
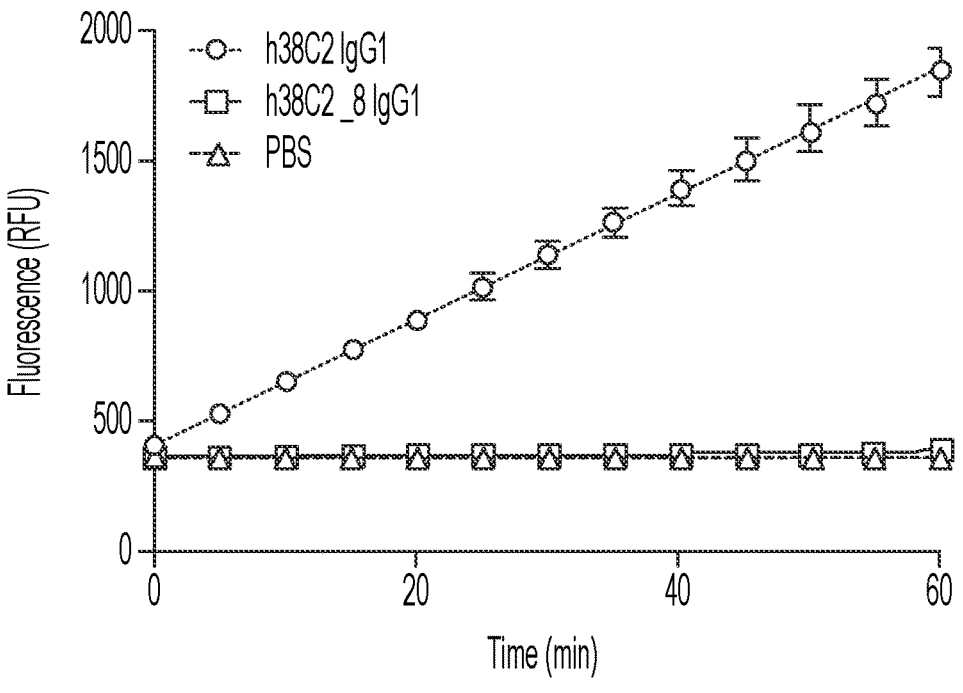
FIG. 6. Assembly and characterization of DVD-ADCs. (A) Structures of the β-lactam hapten derivative of MMAF (compound 7) and the MSPODA derivative of MMAF (compound 8) used in this study. (B) Catalytic activity of h38C2 IgG1 (1 μM) before and after conjugation to 5 equiv of compound 8 (mean±SD of triplicates). (C) MALDI-TOF analysis of the reduced and deglycosylated (PNGase F) compound 8-conjugated anti-HER2 DVD-IgG1. The expected masses for unconjugated heavy and light chains were 63 878 and 36 175 Da, respectively. The expected mass for the heavy chain with one conjugated compound 8 was 64 980 Da. The peak at 34 781 Da corresponds to PNGase F. (D) Comparison of the cytotoxicity of compound 7- (■) and compound 8 (●)-conjugated anti-HER2 DVD-IgG1 following incubation with HER2-positive human SK-BR-3 and KPL-4 cells, and HER2-negative human MDA-MB-231 cells for 72 h at 37° C. Unconjugated anti-HER2 DVD-IgG1 (♦) served as negative control. Mean±SD values of triplicates were plotted.
Figure 6C:
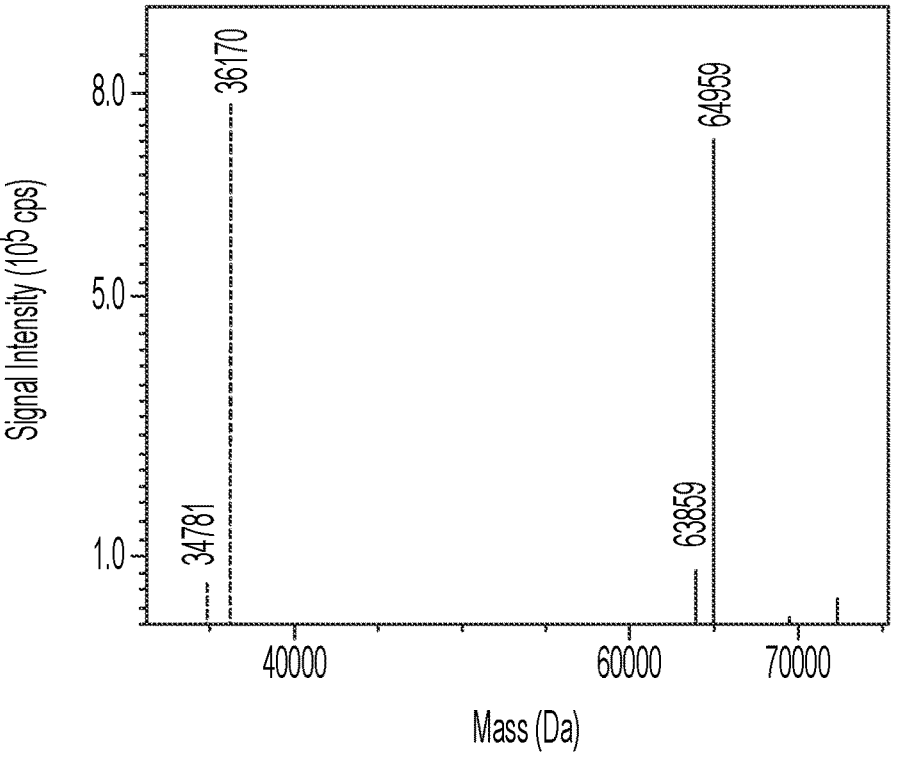
Figure 8B:
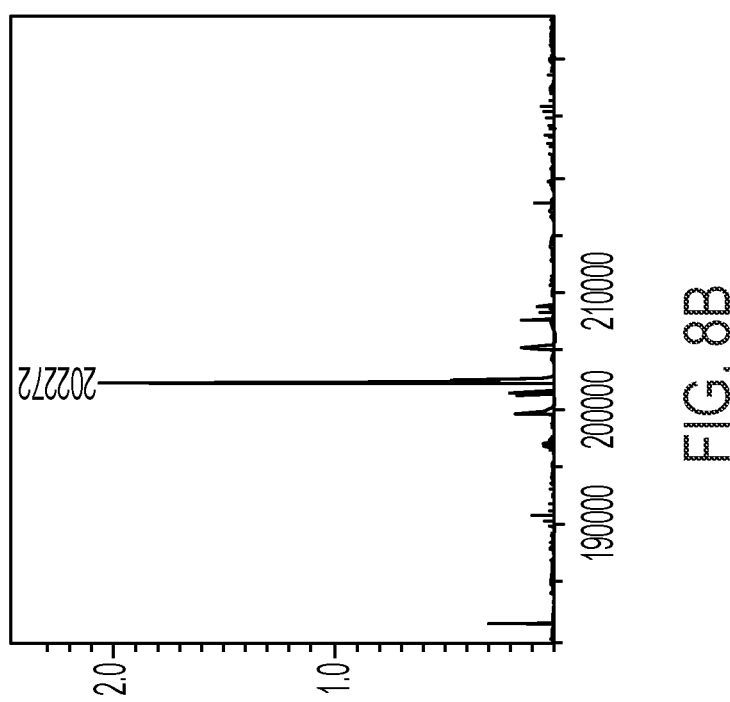
FIG. 8. Mass spectrometry analysis of nonreduced anti-HER2 DVD-ADC. MALDI-TOF analysis of the nonreduced and deglycosylated (PNGase F) unconjugated (A) and compound 8-conjugated (B) anti-HER2 DVD-IgG1. The expected mass for the unconjugated DVD-IgG1 was 200, 106 Da. The expected mass for the DVD-IgG1 with one conjugated compound 8 was 202,310 Da.
Figure 8A:
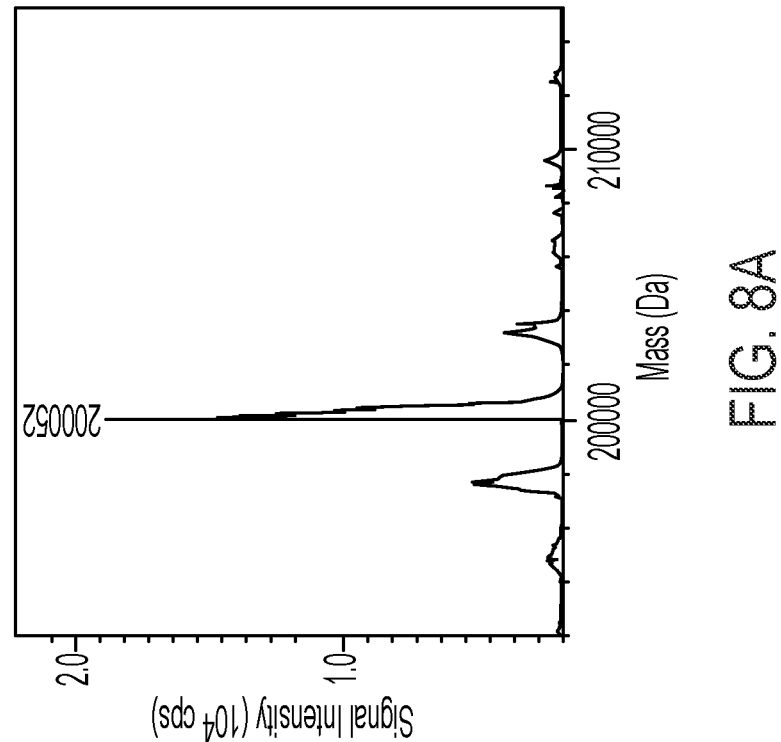

The DVD IgG1 was incubated with compound 7 or 8 as before. Following removal of unconjugated compound, Lys99 conjugation was confirmed by loss of catalytic activity (FIG. 6B). Next, the DVD-ADC assembled via MS-PODA conjugation was analyzed by mass spectrometry. The observed molecular weight of the unconjugated DVD IgG1 after PNGase and DTT treatment was 63,859 Da (heavy chain; expected molecular weight without posttranslational modifications: 63,878 Da) and 36,170 Da (light chain; 36,175 Da). The conjugated DVD IgG1 revealed an increase of the molecular weight of the heavy chain by 1,102 Da, indicating the covalent conjugation of one PODA-MMAF molecule. As noted for the MS-PODA derivative of fluorescein, the conjugation was highly efficient (~95%) and selective without detectable conjugated light chain or multiple conjugated heavy chain (FIG. 6C). In the absence of DTT treatment, the observed molecular weight for the unconjugated and conjugated DVD IgG1 was 200,052 Da and 202,272 Da, respectively, indicating the conjugation of one PODA-MMAF molecule to each of the two reactive Lys99 residues (FIG. 8).

Figure 6D:
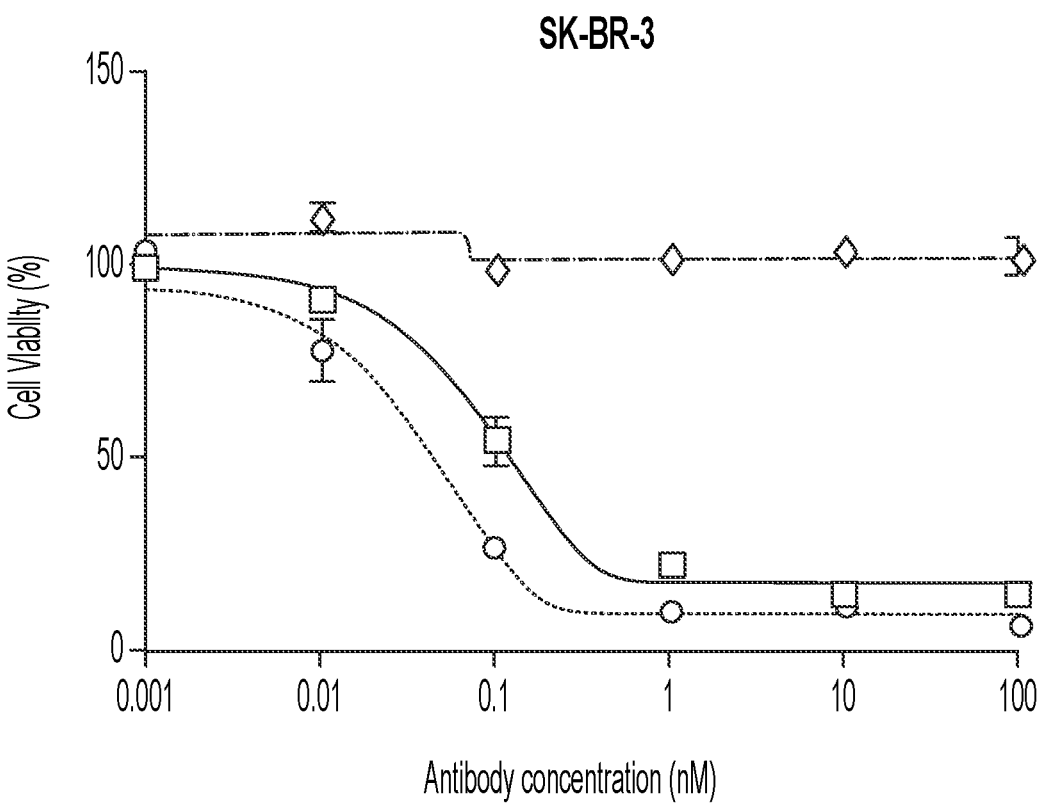
Figure 6D:
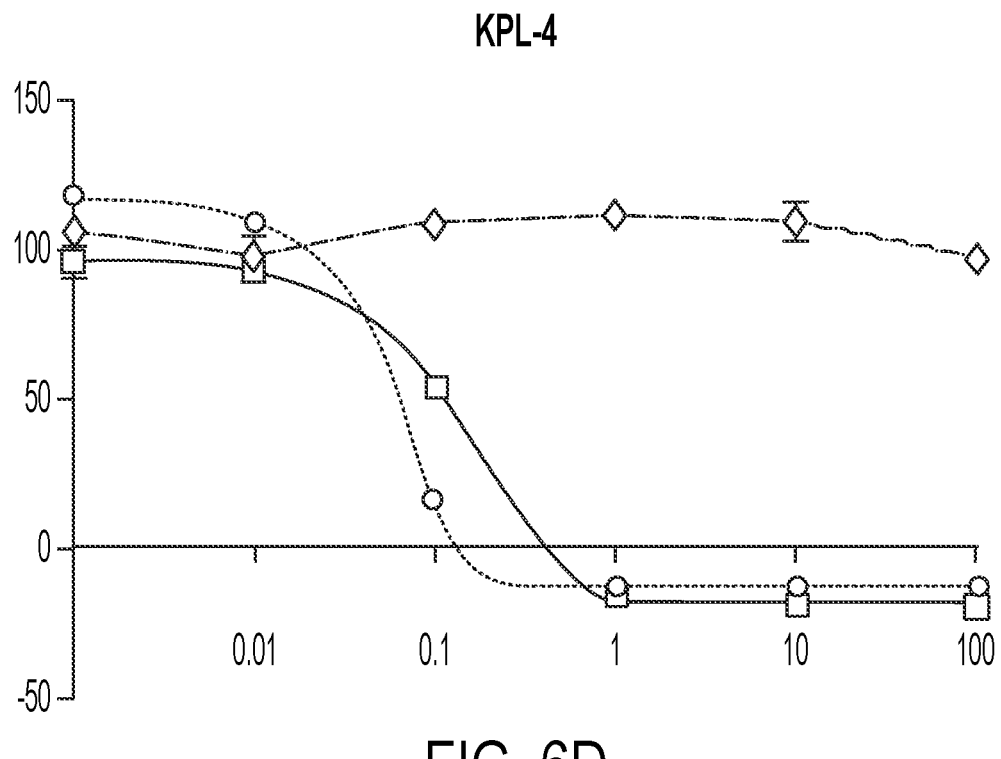
Figure 6D:
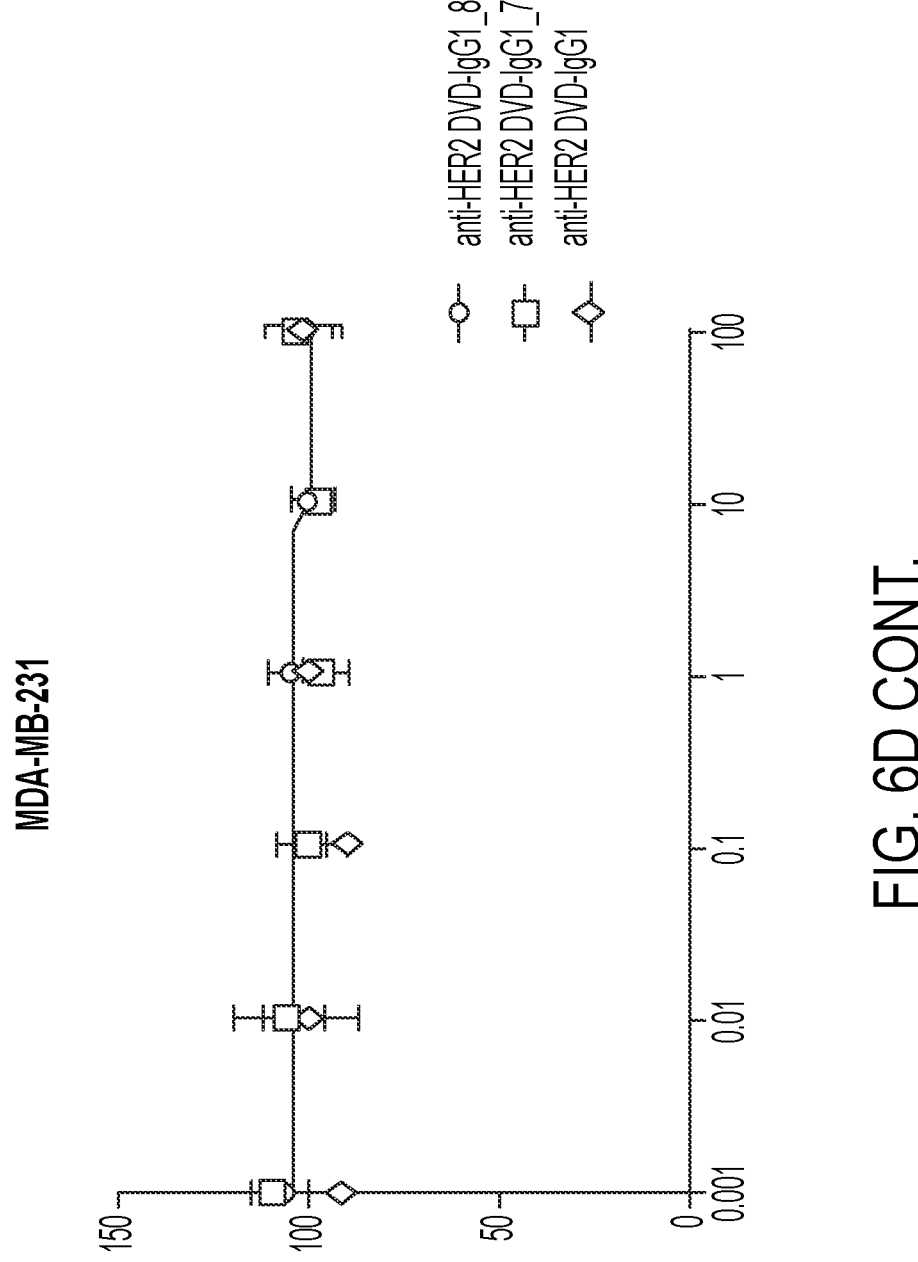

With the homogeneous assembly of the DVD-ADC confirmed, we next tested its ability to mediate potent and selective cytotoxicity. MS-PODA- and β-lactam hapten-assembled DVD-ADCs killed the HER2-positive human breast cancer cell lines SK-BR-3 and KPL-4 with $IC_{50}$ values of 0.21 and 0.34 nM, and 0.1 and 0.09 nM, respectively (FIG. 6D). Neither killed the HER2-negative human breast cancer cell line MDA-MB-231 at up to 100 nM, the highest concentration tested (FIG. 6D). Collectively we conclude that MS-PODA-mediated conjugation of cytotoxic drugs to the two reactive Lys99 residues of DVD IgG1 having an inner h38C2-based Fv is equivalent in quality to DVD-ADCs, which was previously reported employing β-lactam hapten-mediated conjugation (Nanna et al., Nat. Commun. 8, 1112, 2017). Overall, our study establishes a new conjugation chemistry for catalytic antibody h38C2 that is based on arylation of its reactive Lys99 residue and compatible with its therapeutic utilities. This new approach offers distinct synthetic advantages over β-lactam hapten-mediated conjugation strategies.

Example 5 Materials and Methods

Cell lines: Human ovarian cancer cell line IGROV-1 was purchased from American Tissue Culture Collection (ATCC) and cultured in folate deficient RPMI-1640 medium supplemented with 10% (v/v) heat inactivated fetal bovine serum (FBS) and 1× penicillin-streptomycin (containing 100 U/mL penicillin and 100 mg/mL streptomycin; all from Thermo Fisher Scientific). Human T-cell line Jurkat was cultured in RPMI-1640 medium supplemented with 10% (v/v) heat inactivated FBS and 1× penicillin-streptomycin. Human breast cancer cell lines SK-BR-3 and MDA-MB-231 were purchased from ATCC. Human breast cancer cell line KPL-4 was kindly provided by Dr. Naoto T. Ueno based on an MTA with the University of Texas MD Anderson Cancer Center (Houston, TX) and with permission from Dr. Junichi Kurebayashi (Kawasaki Medical School; Kurashiki, Japan). All three cell lines were cultured in DMEM medium supplemented with 10% (v/v) heat inactivated FBS and 1× penicillin-streptomycin. Expi293F cells were cultured in Expi293 expression medium supplemented with 1× penicillin-streptomycin (all from Thermo Fisher Scientific).

Computational modeling: In the crystal structure of h38C2 Fab with a Lys99Arg mutation (PDB ID 6U85), Arg99 was replaced with an azido-$(PEG)_4$-PODA-derivatized Lys residue in silico and subjected to energy minimization using Prime software (Schrödinger) and subjected to molecular dynamics simulations using Desmond software with the OPLS_2005 force field (Schrödinger). The coordinate was solvated in an orthorhombic box of 10 Å each direction with TIP3 water, 150 mM NaCl, and counter ions. The system was pre-equilibrated using the NPT relaxation protocol, which consists of restrained/unrestrained minimizations and short simulations with isothermal and isobaric ensemble. A 10-ns molecular dynamics simulation was done subsequently at constant temperature (300 K) and pressure (1.01325 bar). Simulation quality analysis showed no significant fluctuation of system volume, pressure, temperature, and potential energy during the course of the simulation. Coordinates from the simulation between 1 and 10 ns were used to analyze and identify prominent interactions between the ligand (azido-$(PEG)_4$-PODA) and the antibody (h38C2 Fab). Model figures and atom distances were created and calculated using PyMOL (Schrödinger). (Note: Crystal structure 6U85 is nearly identical to independent crystal structure 6DZR[15] with a root-mean-square deviation (RMSD) of 0.446 Å for 389 Cα atoms; unlike 6DZR, 6U85 does not contain a sulfate ion that forms a salt bridge with Arg99 in the hydrophobic pocket).

Synthesis of MS-PODA and β-lactam hapten derivatives: The syntheses of compounds 1 (MS-PODA-fluorescein), 2 (β-lactam-hapten-TAMRA), 7 (MS-PODA-MMAF), and 8 (β-lactam-hapten-MMAF) are published. The syntheses of compounds 3 (β-lactam-hapten-folate), 4 (β-lactam-hapten-LLP2A), 5 (MS-PODA-folate), and 6 (MS-PODA-LLP2A) and their characterization by $^1$H-NMR, $^{13}$C-NMR, HRMS, and LC-MS are provided in more detail below.

Antibodies: The amino acid sequences of $V_H$ and $V_L$ of h38C2 were published. Purified h38C2 IgG1 was a gift from the laboratory of Carlos F. Barbas III (The Scripps Research Institute; La Jolla, CA). To generate h38C2_Lys99Ala IgG1, light and mutated heavy chain encoding sequences of h38C2 IgG1 were cloned into mammalian expression vector pCEP4 via NheI/XhoI (New England Biolabs). The two plasmids were co-transfected into a density of $3 \times 10^6$ cells/mL of Expi293F cell by using the ExpiFectamine 293 Transfection Kit (Thermo Fisher Scientific) following the manufacturer's instructions. After culturing transfected cells at 37° C., 5% $CO_2$ for 5 days, the culture supernatant was collected and purified by affinity chromatography with a 1-mL HiTrap Protein A column in conjunction with an AKTA FPLC instrument (both from GE Healthcare). The sequences, cloning, expression, and purification of the anti-HER2 DVD-IgG1 were published previously (Nanna, et al., Methods Mol Biol 2033, 39-52, 2019).

Antibody conjugation: 10 µM of h38C2 IgG1 or h38C2_Lys99Ala IgG1 was incubated with 100 µM (5 eq per reactive Lys residue) of compound 1 (MS-PODA-fluorescein) or compound 2 (β-lactam-hapten-TAMRA) in PBS for 3 h at RT. Of the reduced and nonreduced conjugation mixture, 2.5 µg was loaded onto a 10-well NuPAGE 4-12% Bis-Tris Protein Gel (Thermo Fisher Scientific). Fluorescent bands were visualized by blue light on an E-gel Imager and the gel was subsequently stained by PageBlue Protein Staining Solution (all form Thermo Fisher Scientific). Chemically programmed h38C2 IgG1_3, _4, _5, and _6 and the two ADCs (anti-HER2 DVD-IgG1_7 and _8) were assembled analogously, purified with illustra NAP-5 Columns (GE Healthcare), and concentrated with Amicon Ultra 0.5-mL Centrifugal Filters with 30-kDa MWCO.

Mass spectrometry: Unconjugated and conjugated antibodies at 10 µM were reduced with 50 mM DTT in PBS for 10 min at RT followed by enzymatic deglycosylation with PNGase F (New England Biolabs) overnight at 37° C. Following dilution into water, data were obtained on an Agilent Electrospray Ionization Time of Flight (ESI-TOF) mass spectrometer. Deconvoluted masses were obtained using Agilent BioConfirm Software.

Catalytic activity assay: Unconjugated and conjugated antibodies at 1 µM in 98 µL were dispensed into a 96-well plate (Corning) in triplicate. Subsequently, 2 µL of 10 mM methodol was added and the fluorescence (excitation/emission set to 330/452 nm) was measured in 5-min intervals for 1 h at RT using a Spectra Max M5 instrument (Molecular Devices).

Human plasma stability assay: An equal volume of human plasma (Sigma-Aldrich) and 1 mg/mL h38C2 IgG1_1 in PBS were mixed and incubated at 37° C. After 0, 1, 2, 3, 4, 5, 6, 7, and 8 days, 2-µL aliquots were frozen and stored at −80° C. Under reducing condition, aliquots from all time points were analyzed using a 10-well NuPAGE 4-12% Bis-Tris Protein Gel. Fluorescent bands were visualized by blue light on an E-gel Imager and the gel was subsequently stained by PageBlue Protein Staining Solution.

ELISA: 100 ng of Human recombinant folate receptor 1 (FOLR1) diluted at 100 ng/25 µL in Tris-buffered saline (TBS; Bio-Rad) and human recombinant integrin $\alpha_4\beta_1$ (all from R&D systems) diluted at 100 ng/25 µL in TBS supplemented with 1 mM $MnCl_2$ was placed in 96-well half-area microplates (Corning) and incubated at 4° C. overnight. After 1-h blocking with 3% (v/v) skim milk in TBS, 5 µg/mL of unconjugated h38C2 IgG1 and h38C2 IgG1 chemically programmed with folate (compounds 3 and 5) or LLP2A (compounds 4 and 6) were added to the FOLR1- or integrin $\alpha_4\beta_1$-coated wells, respectively, and incubated for 1 h. Subsequently, the wells were washed 3 times with 0.05% (v/v) Tween 20 (Sigma-Aldrich) in TBS. A 1:2,000 dilution of HRP-conjugated goat anti-human IgG Fcγ-specific pAbs (Jackson ImmunoResearch) in 3% (v/v) skim milk in TBS was added and incubated for 1 h at RT. Following 3 washes as before, BioFX ABTS One Component HRP Microwell Substrate (Surmodics) was added to the wells following the manufacturer's instructions. Absorbance at 405 nm was detected using a Spectra Max M5 instrument. The experiment was performed in triplicate.

Flow cytometry analysis: IGROV-1 cells ($1\times10^5$) were incubated with h38C2 IgG1 chemically programmed with folate (compounds 3 and 5) diluted in 1% (v/v) BSA in TBS with 0.02% sodium azide (FACS buffer) for 1 h at RT. In parallel, an equal number of Jurkat cells was incubated with h38C2 IgG1 chemically programmed with LLP2A (compounds 4 and 6) in FACS buffer supplemented with 1 mM $MnCl_2$. Following 3 washes with FACS buffer, a 1:1,000 dilution of FITC-conjugated goat anti-human IgG Fcγ-specific pAbs (Jackson ImmunoResearch) in FACS buffer was added to the cells and incubated for 1 h. Following 3 washes as before, the cells were suspended in 4% (w/v) paraformaldehyde (Alfa Aesar) in PBS and flow cytometry was performed on a BD FACSCanto instrument. Data were analyzed with FlowJo software (Tree Star).

Cytotoxicity assay: Following a previously published procedure (Hwang et al., Cell Chem Biol. 26:1229-1239, 2019), SK-BR-3 ($5\times10^3$ per well), MDA-MB-231 ($3\times10^3$ per well), and KPL-4 ($3\times10^3$ per well) were plated in 96-well tissue culture plates. Ten-fold serially diluted (0.001-100 nM) ADCs (anti-HER2 DVD-IgG1_7 and _8) along with anti-HER2 DVD-IgG1 as negative control were added to the wells and incubated at 37° C. in an atmosphere of 5% $CO_2$ for 72 h. Subsequently, cell viability was measured using CellTiter 96 Aqueous One Solution (Promega) following the manufacturer's instructions and plotted as a percentage of untreated cells. $IC_{50}$ values (mean±SD) were calculated by GraphPad Prism software.

Synthesis of MS-PODA and β-Lactam Hapten Derivatives of Folate and LLP2A:

General methods: All experiments involving moisture-sensitive compounds were conducted under anhydrous conditions (positive argon pressure) using standard syringe, cannula, and septa apparatus. Commercial reagents were purchased from Sigma-Aldrich, TCI America, Acros, Chem-Impex, Ambeed, and Novabiochem. All solvents were purchased in anhydrous form (Sigma-Aldrich) and used without further drying. HPLC-grade hexanes, ethyl acetate (EtOAc), dichloromethane (DCM), and methanol were used in chromatography. Silica gel column chromatography employed a Teledyne CombiFlash Rf 200i instrument with either hexane/EtOAc or DCM/methanol gradients. NMR spectra were recorded using a Varian Inova 400 MHz instrument. Coupling constants are reported in Hertz (Hz), and peak shifts are reported in δ (ppm) relative to $CDCl_3$ ($^1H$ 7.26 ppm, $^{13}C$ 77.16 ppm). Low-resolution mass spectra (ESI) were measured with an Agilent 1200 series LC/MSD-SL system. High resolution mass spectra (HRMS) were obtained by positive ion, ESI analysis on a Thermo Fisher Scientific LTQ Orbitrap XL mass spectrometer with HPLC sample introduction using a short narrow-bore C18 reversed-phase (RP) column with acetonitrile (MeCN)—$H_2O$ gradients. Preparative HPLC purification was performed using a Waters 2545 binary pump (MeCN/$H_2O$ gradient) with a Phenomenex Gemini-Cis (5 μm, 250×21 mm) preparative column and UV detection at 210 nm.

Semi-preparative HPLC purification was performed using an Agilent 1200 series quaternary pump (MeCN/$H_2O$ gradient) with a Phenomenex Kinetix-$C_{18}$ (5 μm, 250×10 mm) semi-preparative column, 3 mL/min flow rate, and UV detection at 210 nm. Analytical HPLC analyses of purified peptides were performed using an Agilent 1200 series quaternary pump (MeCN/$H_2O$ gradient) with a Phenomenex Gemini-Cis (5 μm, 250×4 mm) analytical column, 1 mL/min flow rate, and UV detection at 210 nm.

Figure 9A:
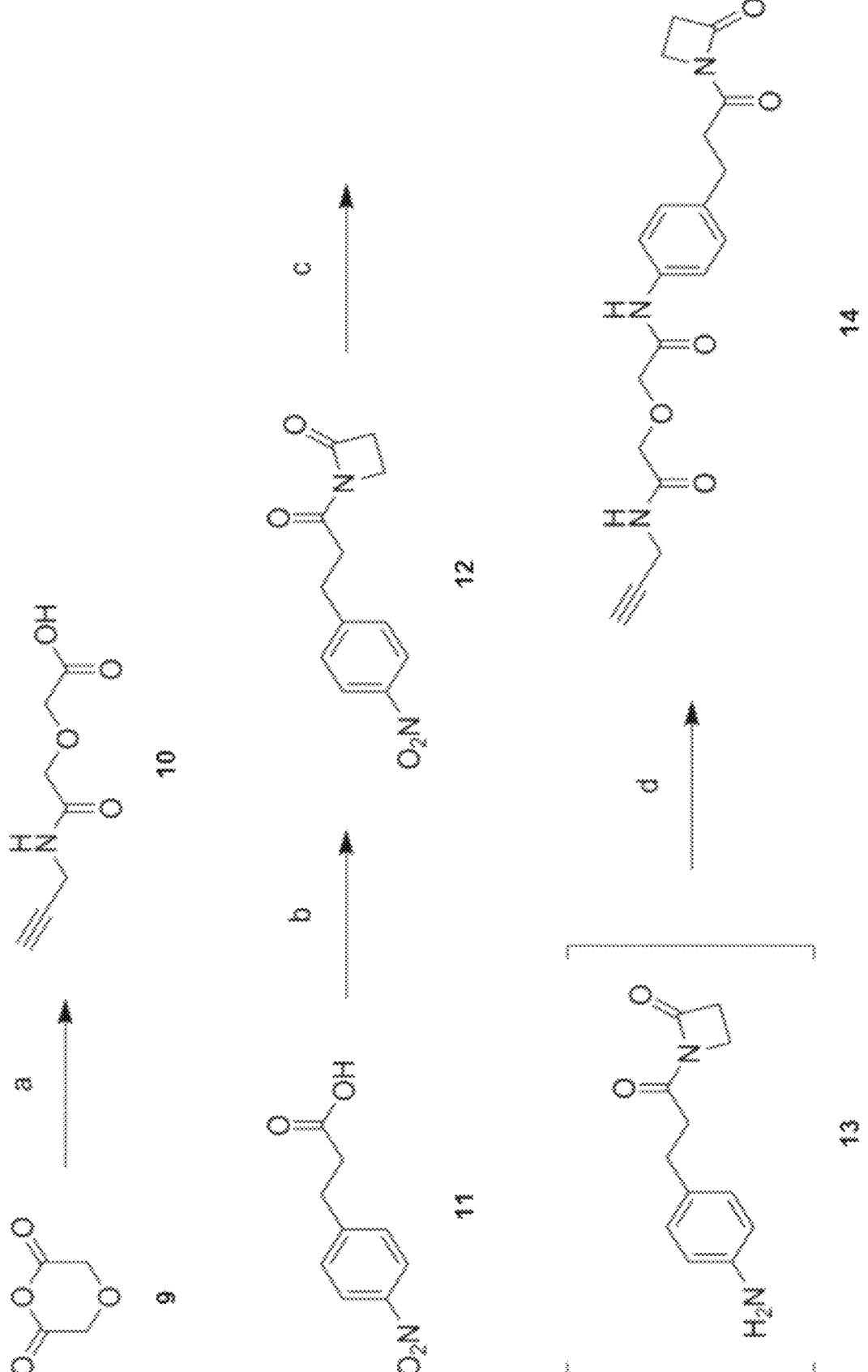
FIGS. 9A-9C. 9A. Scheme 1. Synthesis of compound 14. (a) Propargylamine, THF, RT, 1 d, 43%; (b) thionyl chloride, 0° C. to 60° C., 1.5 h then azetidin-2-one, n-BuLi, THF, −78° C. to RT, overnight, 24%; (c) Pd/C, H$_2$, EtOAc, RT, 6 h; (d) 10, EDC·HCl, HOBt·H$_2$O, DMF, 2.5 h, 59% (2 steps from 12). 9B. Spectrum 1. $^1$H-NMR of compound 14. 9C. Spectrum 2. $^{13}$C-NMR of compound 14.
Figure 9B:
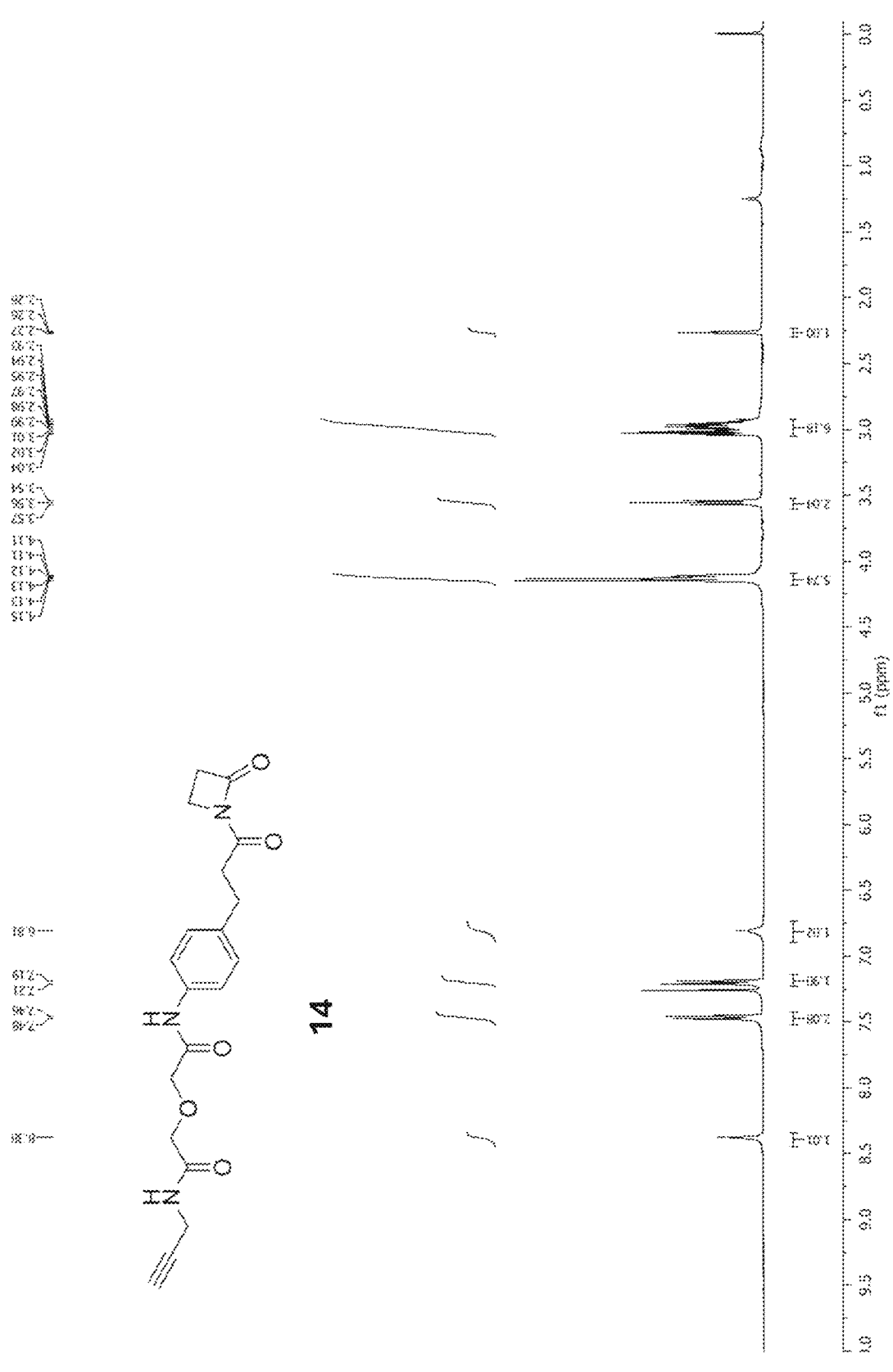
Figure 9C:
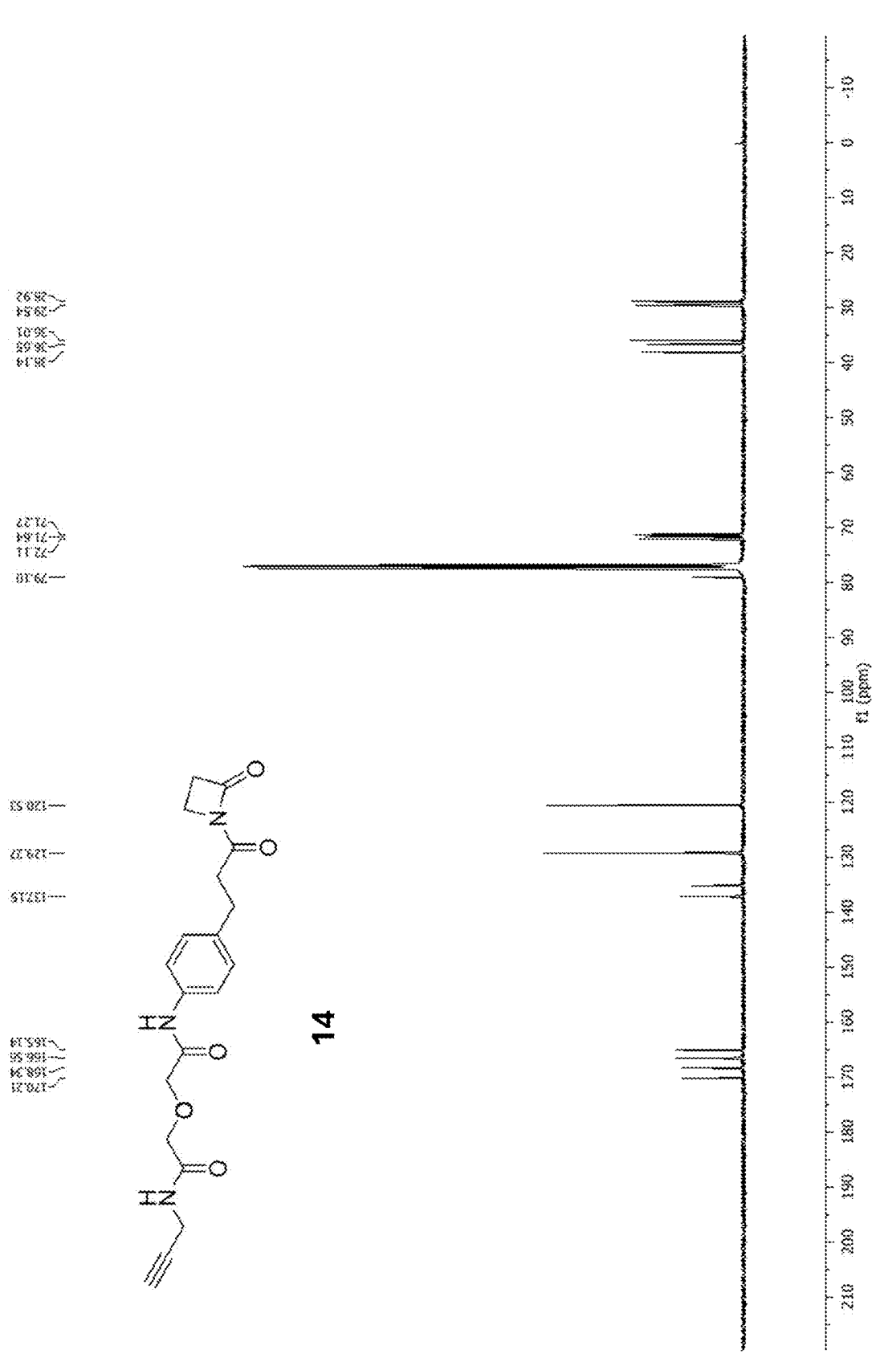

Synthesis of 2-(2-oxo-2-((4-(3-oxo-3-(2-oxoazetidin-1-yl) propyl) phenyl) amino) ethoxy)-N-(prop-2-yn-1-yl)acetamide (14): The synthesis of β-lactam-hapten-alkyne 14 was achieved by coupling compounds 10 and 13 (FIG. 9A Scheme 1). Compound 10 was prepared by treatment of diglycolic anhydride 9 with propargylamine. Compound 12 was synthesized according to literature procedures (Magano et al., Org. Process Res. Dev. 18, 142-151, 2014), hydrogenated to the corresponding aniline-containing 13 and then subsequently used for coupling with 10 to afford 14. In detail, to a solution of 1-(3-(4-nitrophenyl)propanoyl)azetidin-2-one (12) (100 mg, 0.40 mmol) in EtOAc (15 mL) was added Pd/C (10% (w/w), 43 mg, 0.040 mmol). The mixture was degassed in vacuo and then the vessel was charged with $H_2$. After stirring at RT for 6 h, the mixture was filtered through Celite and the filtrate was concentrated in vacuo. To a solution of the resulting crude 13 in dimethylformamide (DMF; 15 mL) was added hydroxybenzotriazole hydrate (HOBt·$H_2O$; 80 mg, 0.52 mmol), 10 (76 mg, 0.44 mmol), and 1-ethyl-3-(3-dimethylaminopropyl) carbodiimide hydrochloride (EDC·HCl; 85 mg, 0.44 mmol) and the mixture was stirred at RT for 2.5 h. DMF was removed by evaporation, $H_2O$ was added, and the mixture was extracted 3 times with chloroform ($CHCl_3$). The organic layer was washed with brine, dried ($Na_2SO_4$) and the crude material was purified by silica gel CombiFlash chromatography (hexane/EtOAc gradient, 0-100% over 30 min) to afford 14 as an off-white powder (89 mg, 59%, 2 steps from 12).FIG. 9B $^1H$ NMR (400 MHz, chloroform-d) δ 8.38 (s, 1H), 7.47 (d, J=8.4 Hz, 2H), 7.20 (d, J=8.4 Hz, 2H), 6.81 (s, 1H), 4.15-4.11 (m, 6H), 3.56 (t, J=5.3 Hz, 2H), 3.04-2.93 (m, 6H), 2.26 (t, J=2.5 Hz, 1H). FIG. 9C $^{13}C$ NMR (101 MHz, chloroform-d) δ 170.21, 168.34, 166.56, 165.14, 137.15, 135.19, 129.27, 120.53, 79.10, 72.11, 71.64, 71.27, 38.14, 36.65, 36.01, 29.54, 28.92. HR-MS (ESI+) calculated for $C_{19}H_{22}N_3O_5$: 372.1554 [M+H]$^+$; found: 372.1552.

General procedure for solid-phase peptide synthesis (SPPS): SPPS resin was pre-swollen in N-methyl-2-pyrrolidone (NMP) with shaking (20 min). Sieber Amide resin (Novabiochem, 0.71 mmol/g) was utilized for certain peptides and the loading procedure is described where applicable. On-resin fluorenylmethyloxycarbonyl (Fmoc) deprotection was achieved using 20% (v/v) piperidine in DMF with shaking (10 min). Fmoc-protected amino acids (2.0-4.0 eq based on resin) were dissolved in NMP and pre-activated by the addition of HATU (0.95 mole-eq relative to the amino acid) and DIEA (2.0 mole-eq relative to the amino acid) with shaking (1 min). The resin was washed with NMP, and the solution of HATU-activated amino acid was added to the washed resin. Coupling reactions were shaken at RT and allowed to proceed from 2 h to overnight, depending on the eq used and steric bulk of the amino acid. Coupling reactions were routinely checked for completion using a Kaiser test. Once completed, the resin was filtered and washed with NMP, followed by Fmoc-deprotection using 20% (v/v) piperidine in DMF with shaking (10 min). Cleavage of the Lys ε-amine Dde group was performed by treatment with 2% (v/v) hydrazine monohydrate in NMP (2 h, twice) with allyl alcohol (200 eq based on resin) for peptides 17 and 6. Deprotection of the Lys ε-amine Alloc group was performed by treatment with Pd(PPh$_3$)$_4$ (0.30 eq based on resin) and PhSiH$_3$ (10 eq based on resin) in CHCl$_3$, which was well-degassed by bubbling with argon gas (20 min, 3 times). Following Alloc-deprotection, the resin was treated with 0.50% (w/v) sodium diethyldithiocarbamate trihydrate in DMF (20 min, 3 times) to scavenge residual Pd metal. Coupling with diglycolic anhydride 9 was performed in the presence of N, N-diisopropylethylamine (DIEA; 4.0 eq based on resin) in NMP (3 h) and the resin was subsequently coupled with 4-(5-(methylsulfonyl)-1,3,4-oxadiazol-2-yl) aniline (18, Ambeed, 2.0 eq based on resin) using HATU (0.95 mole-eq relative to the amino acid) and DIEA (2.0 mole-eq relative to the amino acid) with shaking (RT, 3 to 4 h). Cleavage of the finished resin with global deprotection was performed using a cocktail of trifluoroacetic acid (TFA)/triisopropylsilane (TIPS)/H$_2$O=95:2.5:2.5 (4.0 mL, 2 h). The mixture was filtered, and the filtrate was added to cold diethyl ether (Et$_2$O). The resulting precipitate was washed with cold Et$_2$O (3 times). Crude peptides were dissolved in 0.1% TFA containing MeCN and H$_2$O and purified using preparative RP-HPLC. Further purification was conducted using semi-preparative RP-HPLC when needed. HPLC eluents were A: 0.1% TFA in H$_2$O; B: 0.1% TFA in MeCN.

General procedure for Cu-catalyzed azide-alkyne cycloaddition reactions: Azido-containing peptides targeting either FOLR1 or integrin α$_4$β$_1$ (1.0 eq) were dissolved in H$_2$O (5.0 mM) and mixed with 14 (1.1 eq) in DMSO (5.0 mM based on the peptide). Separately, 4.0% (w/v) CuSO$_4$.5H$_2$O in H$_2$O (0.13 eq), 0.10 M tris[(1-benzyl-1H-1,2,3-triazol-4-yl)methyl]amine (TBTA) in DMSO (0.25 eq), and 0.50 M sodium ascorbate in H$_2$O (5.0 eq) were combined and the mixture was added to the peptide solution and incubated in the dark (1 to 6 d). The resulting crude peptide was purified using preparative RP-HPLC using gradients consisting of A: 0.1% TFA in H$_2$O; B: 0.1% TFA in MeCN.

Figure 10A:
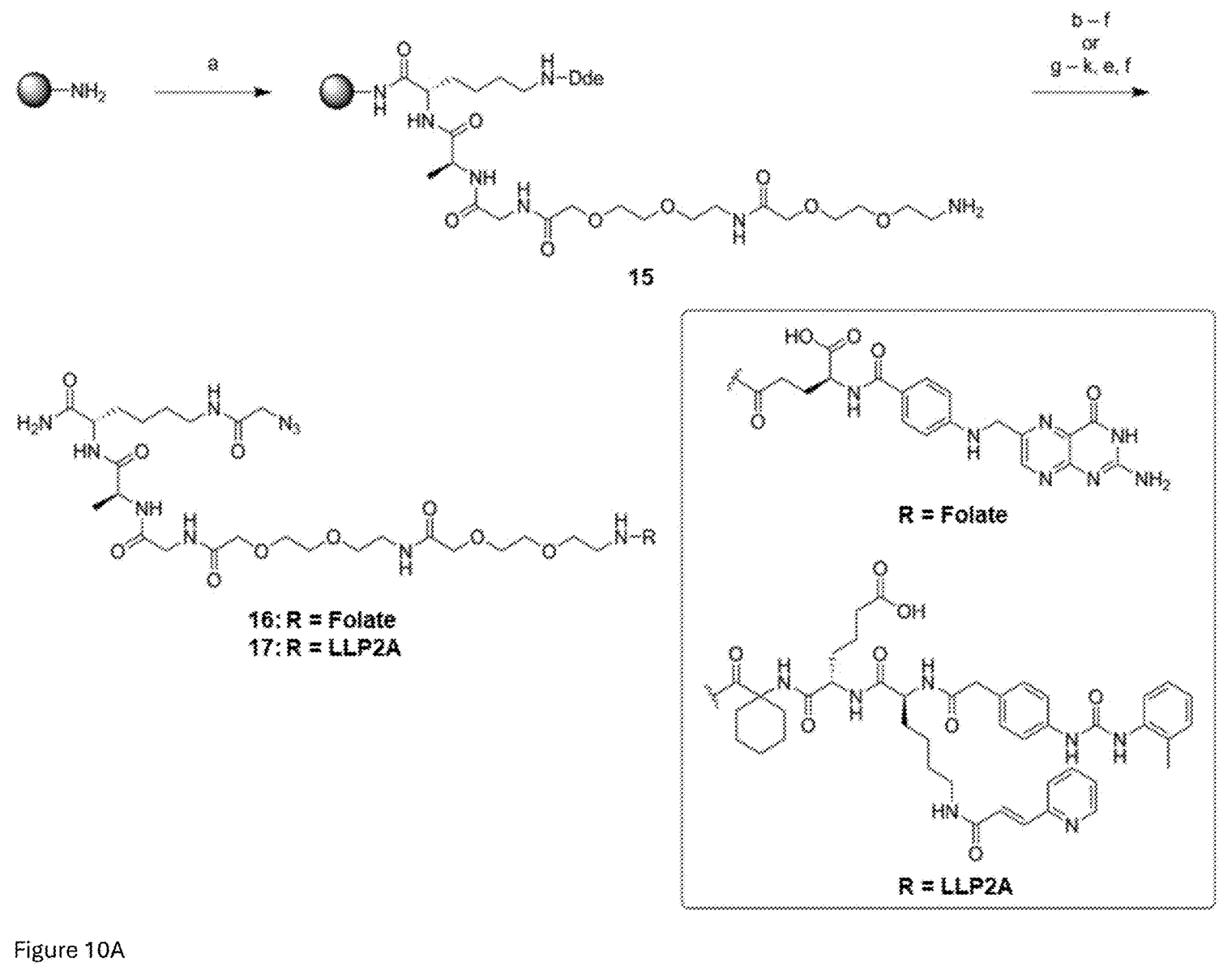
Figure 10B:
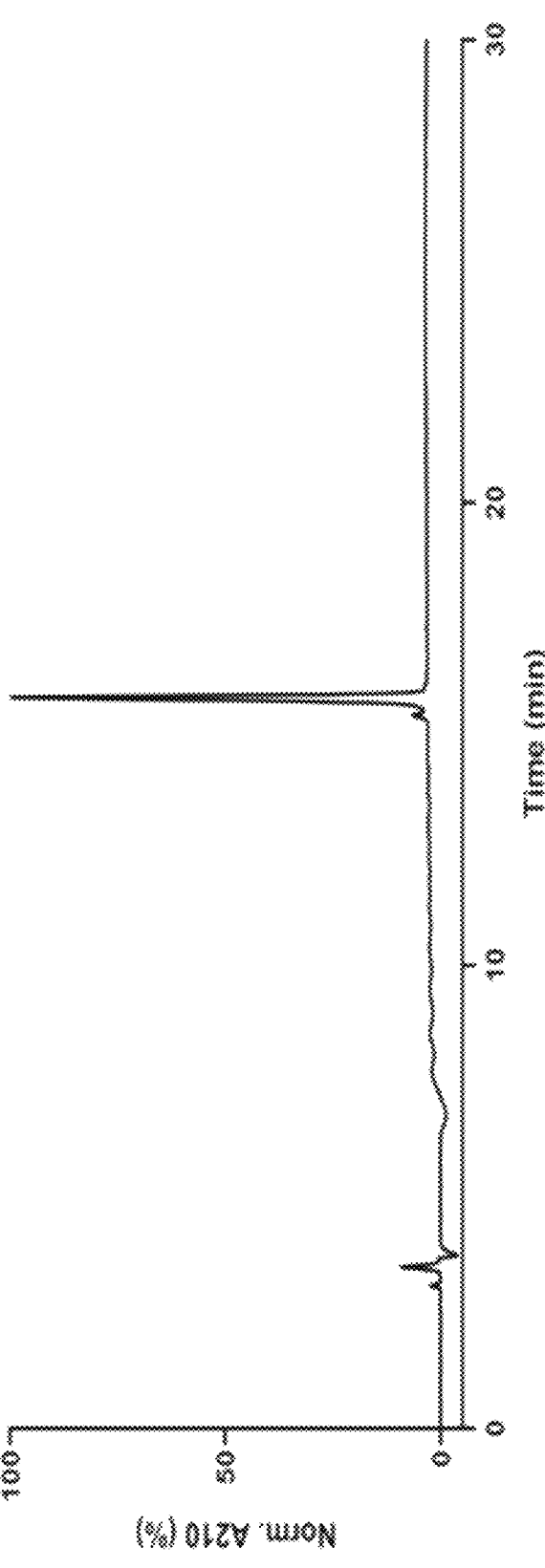
Figure 10C:
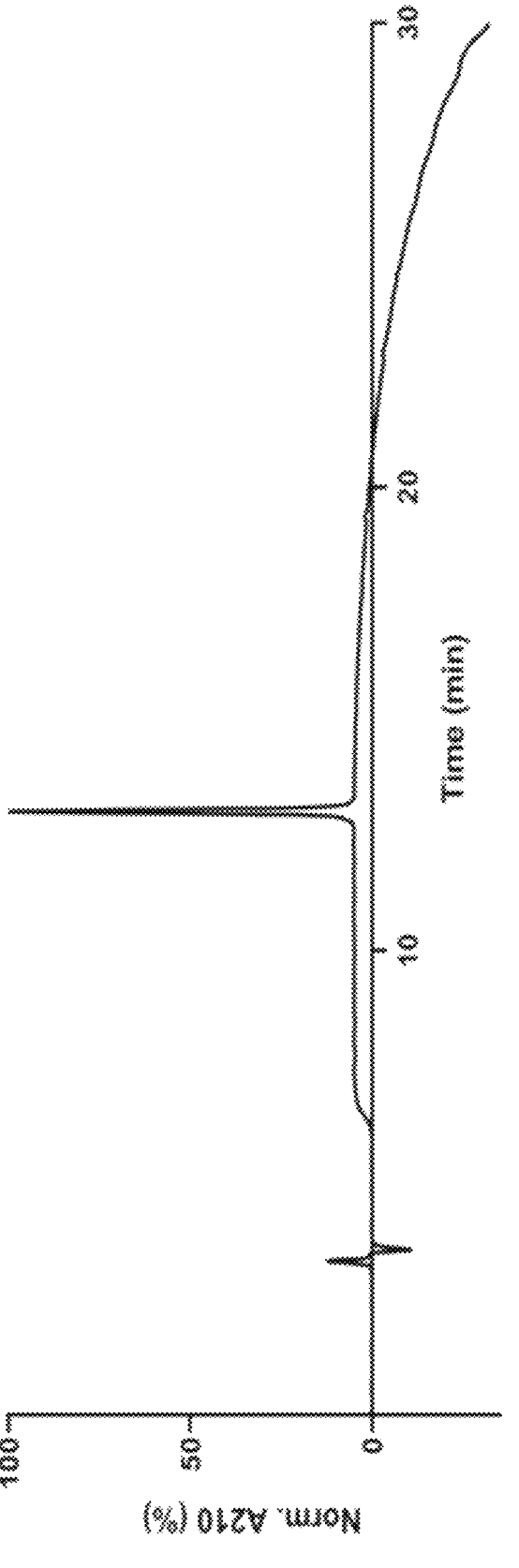

Synthesis of azido-folate and azido-LLP2A peptides: The synthesis of azido peptides targeting either FOLR1 or integrin α$_4$β$_1$ were conducted using standard Fmoc-based solid phase peptide synthesis (SPPS) protocols using Fmoc-L-Lys (Dde)-OH, which can be selectively deprotected by treatment with hydrazine and functionalized at the final step of peptide resin construction (FIG. 10A Scheme 2). Folate-containing peptide (16) was synthesized from Sieber Amide resin (Novabiochem, 0.71 mmol/g)-bound peptide (15) using a TFA-protected pteroic acid analog having an α-protected glutamic acid residue.[2] Following removal of the Lys ε-amine Dde protecting group with 2% (v/v) hydrazine monohydrate in NMP, the azide group was incorporated by coupling with azidoacetic acid. The finished resin was cleaved with a TFA cocktail and purified by RP-HPLC (FIG. 10B) to afford 16 (FIG. 10A Scheme 2). The LLP2A-containing peptide (17) was synthesized from Sieber Amide resin (Novabiochem, 0.71 mmol/g)-bound peptide (15) by sequentially coupling with Fmoc-1-aminocyclohexane carboxylic acid (Fmoc-Ach-OH), Fmoc-L-α-aminoadipic acid δ-tert-butyl ester (Fmoc-L-Aad(Ot-Bu)-OH), and Fmoc-L-Lys (Alloc)-OH. The resulting resin was coupled with 4-(N'-(2-methylphenyl)urea)phenylacetic acid (MPUPA) NHS ester, and then the Alloc group was selectively removed by treatment with Pd(PPh$_3$)$_4$/PhSiH$_3$, followed by coupling with trans-3-(3-pyridyl)-acrylic acid (Agarwal et al., Bioconjug. Chem. 26, 176-192, 2015). The Lys ¿-amine Dde protecting group was removed by treating with 2% (v/v) hydrazine in NMP in the presence of allyl alcohol (200 eq) to avoid undesired hydrogenation of acrylic acid moiety (Wagner et al., Science 278, 2085-2092, 1995). The azide group was subsequently incorporated by treatment with azidoacetic acid and the finished resin was treated with a TFA cocktail and purified by RP-HPLC (FIG. 10C) to obtain peptide (17) (FIG. 10A Scheme 2).

Figure 11A:
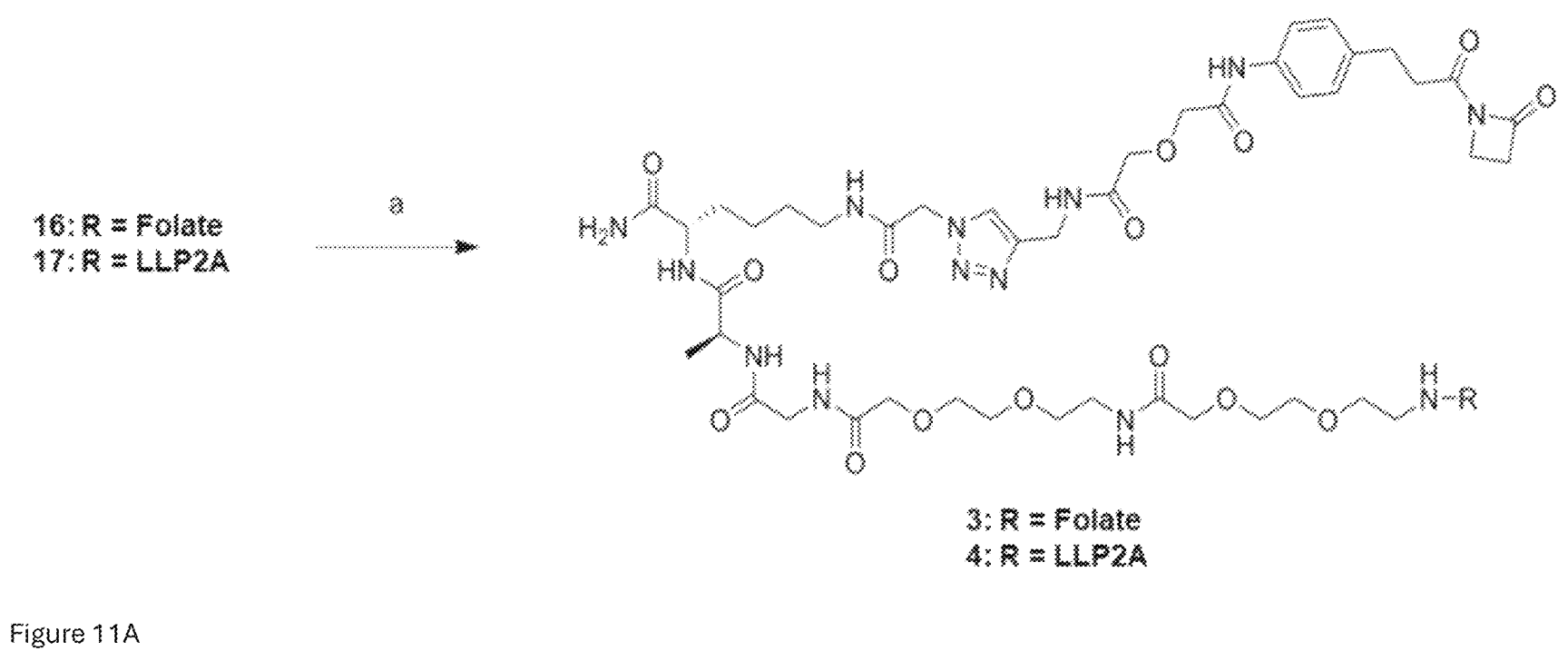
Figure 11B:
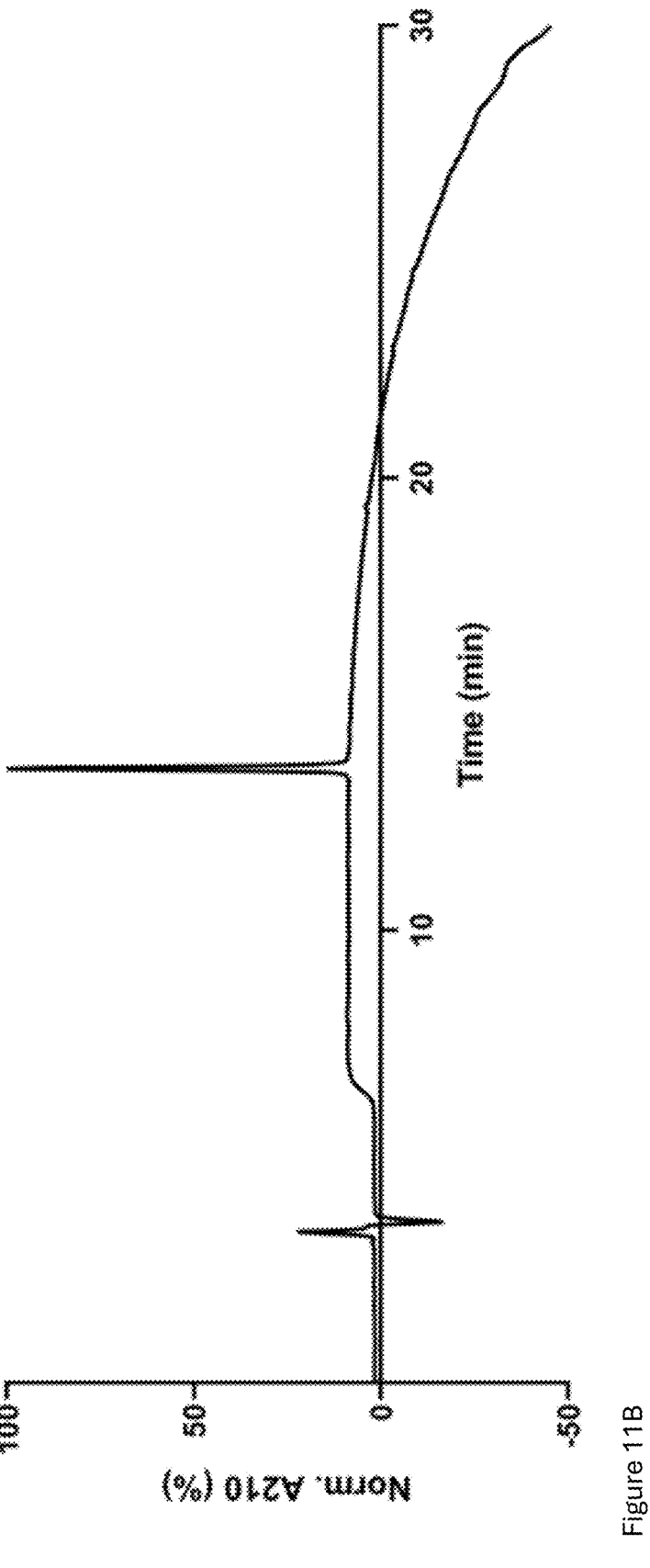
Figure 11C:
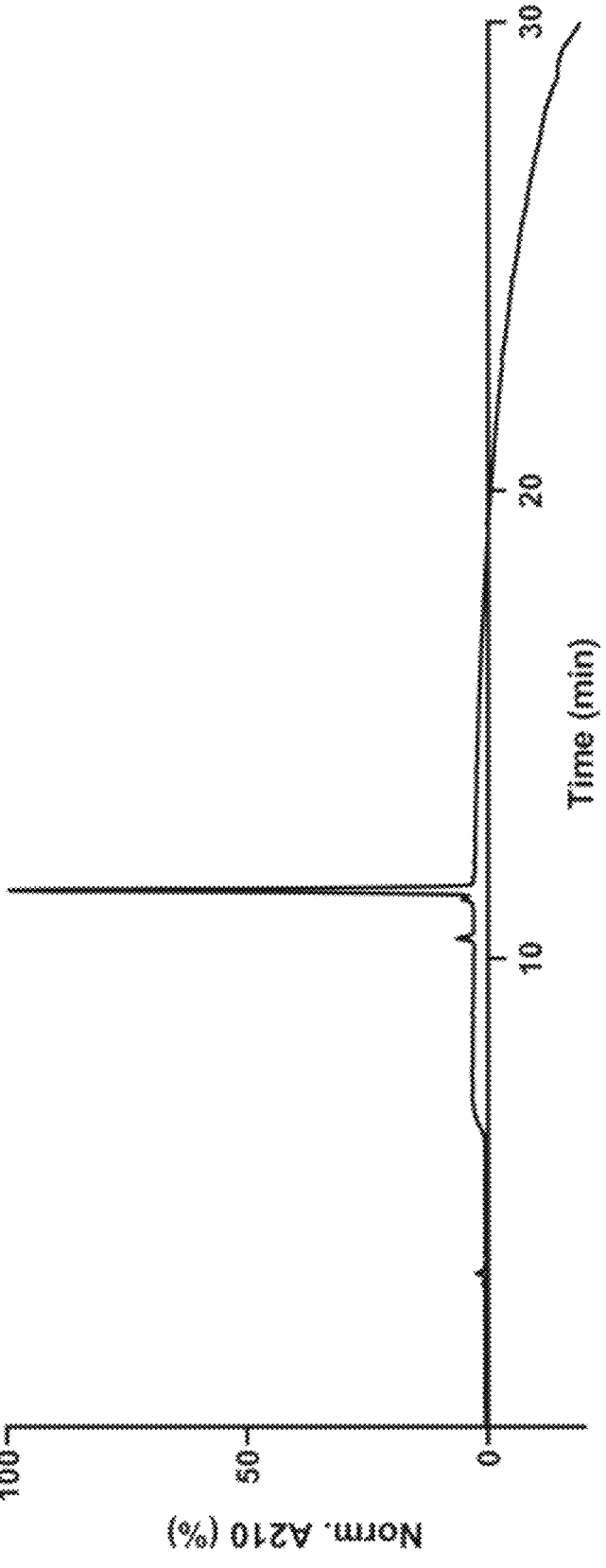

Synthesis of β-lactam-hapten-folate 3 and β-lactam-hapten-LLP2A 4: Compounds 3 and 4 (FIG. 4) were synthesized utilizing Cu-catalyzed azide-alkyne cycloaddition reactions of azido peptides 16 and 17, respectively, and 14 (FIG. 11A Scheme 3). (FIGS. 11B-11C)

Figure 12A:
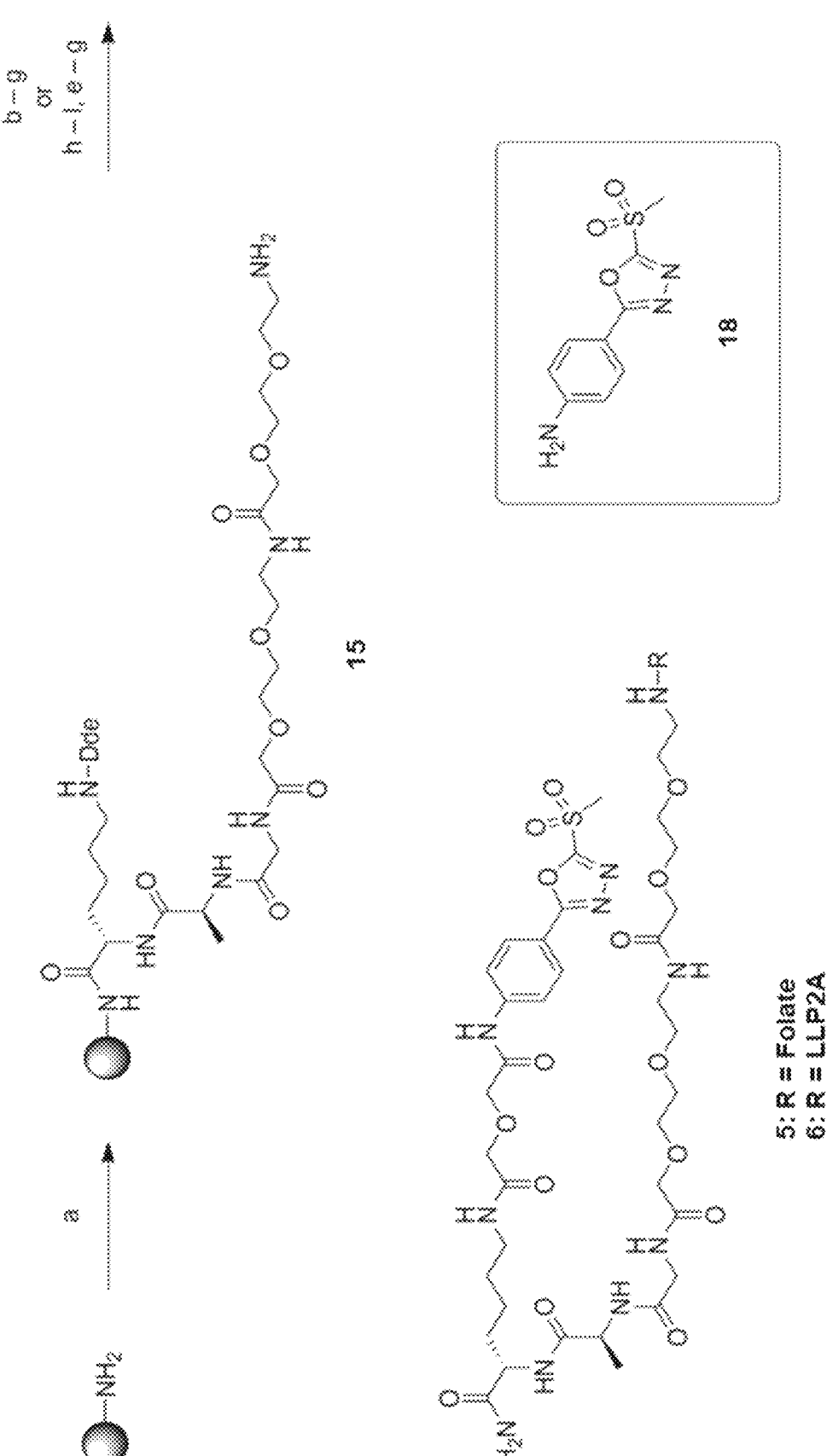
FIGS. 12A-12C. 12A. Scheme 4. Synthesis of MS-PODA-folate 5 and MS-PODA-LLP2A 6. (a) Fmoc-SPPS; (b) Fmoc-L-Glu(OH)-Ot-Bu, HATU, DIEA, NMP then 20% (v/v) piperidine in DMF; (c) N-10-TFA-pteroic acid, HATU, DIEA, NMP; (d) 2% (v/v) hydrazine monohydrate in NMP; (e) diglycolic anhydride, DIEA, NMP; (f) 18, HATU, DIEA, NMP; (g) $TFA/TIPS/H_2O=95:2.5:2.5$; (h) Fmoc-SPPS using Fmoc-Ach-OH, Fmoc-L-Adp(Ot-Bu)-OH, and Fmoc-L-Lys(Alloc)-OH; (i) MPUPA-NHS ester, DIEA, NMP; (j) $Pd(PPh_3)_4$, $PhSiH_3$, $CHCl_3$; (k) trans-3-(3-pyridyl)-acrylic acid, HATU, DIEA, NMP; (l) 2% (v/v) hydrazine monohydrate in NMP, allyl alcohol. 12B. Chromatogram 5. Analytical HPLC of MS-PODA-folate 5. 12C. Chromatogram 6. Analytical HPLC of MS-PODA-LLP2A 6.
Figure 12B:
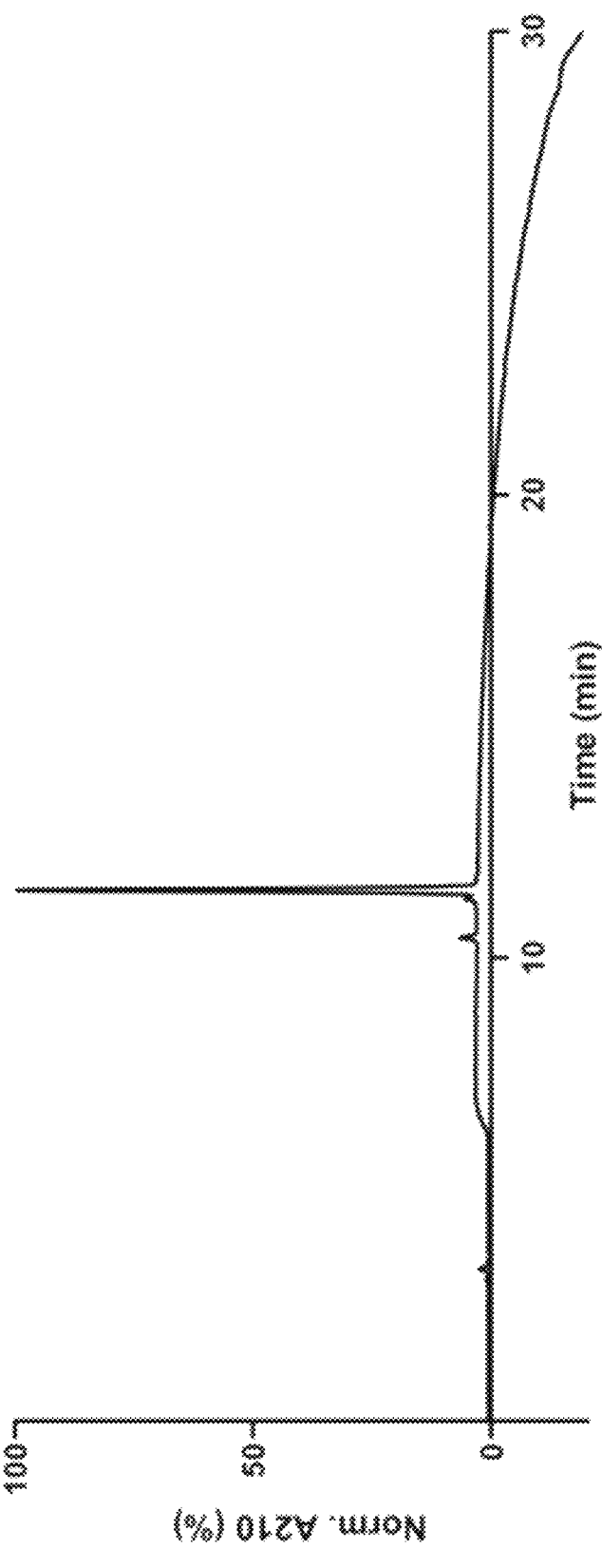
Figure 12C:
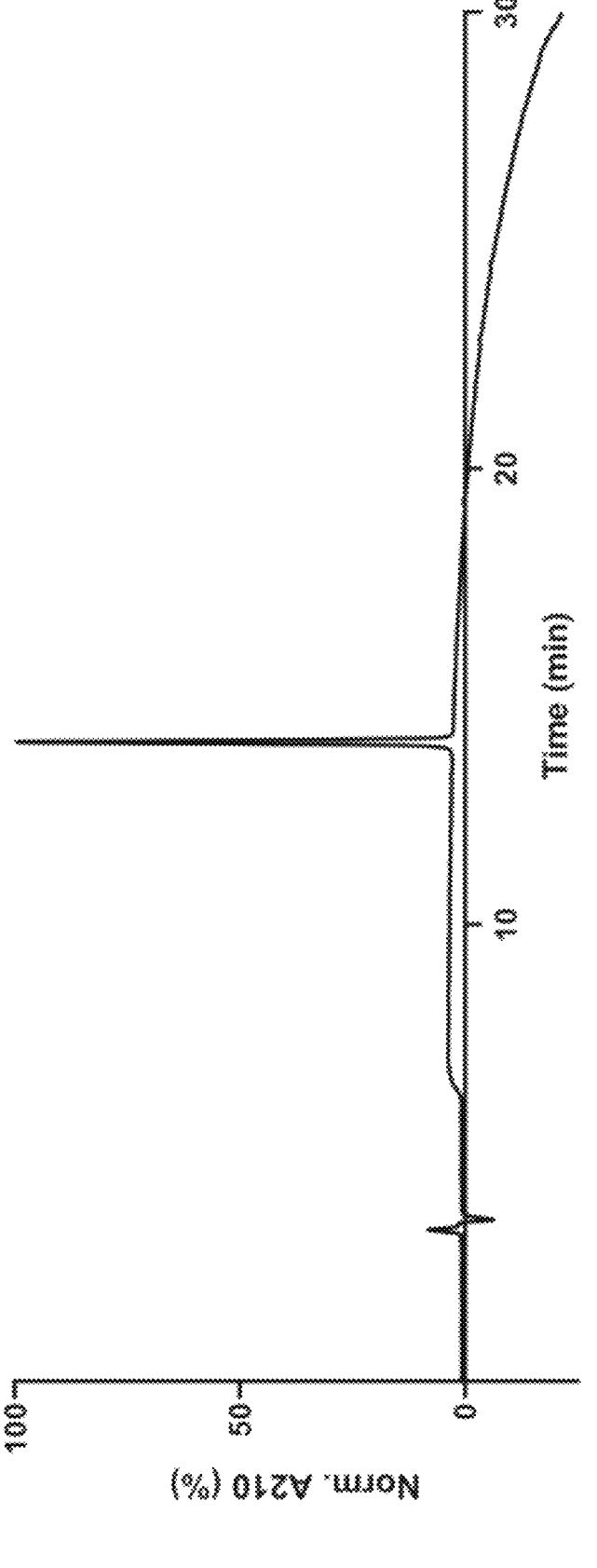

Synthesis of MS-PODA-folate 5 and MS-PODA-LLP2A 6: Compounds 5 and 6 (FIG. 4) were synthesized by procedures described above for the synthesis of 16 and 17, except that following the removal of the Lys ε-amine Dde protecting group, coupling was performed with the diglycolic anhydride 9 and the commercially available MS-PODA aniline derivative 18 rather than with azidoacetic acid NHS ester (FIG. 12A Scheme 4). (FIGS. 12B-12C)

The invention thus has been disclosed broadly and illustrated in reference to representative embodiments described above. It is understood that various modifications can be made to the present invention without departing from the spirit and scope thereof. It is further noted that all publications, patents and patent applications cited herein are hereby expressly incorporated by reference in their entirety and for all purposes as if each is individually so denoted. Definitions that are contained in text incorporated by reference are excluded to the extent that they contradict definitions in this disclosure.

---

What is claimed is:

1. A catalytic antibody comprising a heavy chain variable domain of SEQ ID NO:4 and a light chain variable domain of SEQ ID NO:3 wherein residue Lys99 of the heavy chain variable domain is heteroarylated.

2. The catalytic antibody of claim 1, wherein the heteroarylated Lys99 is phenyloxadiazole Lys99.

3. An antibody-agent conjugate, comprising a catalytic antibody comprising a heavy chain variable domain of SEQ ID NO:4 and a light chain variable domain of SEQ ID NO:3 wherein residue Lys99 of the heavy chain variable domain is heteroarylated and an agent moiety, wherein the agent moiety is conjugated to the heteroarylated Lys99 of the heavy chain variable domain.

4. The antibody-agent conjugate of claim 3, wherein the catalytic antibody is IgG1 or Fab.

5. The antibody-agent conjugate of claim 3, wherein heteroarylated Lys99 is phenyloxadiazole Lys99.

6. The antibody-agent conjugate of claim 3, where the agent moiety is a drug moiety or a cytotoxic agent.

7. The antibody-agent conjugate of claim 6, wherein the drug moiety is MMAF.

8. The antibody-agent conjugate of claim 6, which is a dual variable domain antibody drug conjugate (DVD-ADC).

9. The antibody-agent conjugate of claim 8, comprising a variable domain that specifically targets a tumor antigen.

10. The antibody-agent conjugate of claim 3, wherein the agent moiety is a targeting moiety.

11. The antibody-agent conjugate of claim 10, wherein the targeting moiety is folate or LLP2A.

12. A method for conjugating an agent to a catalytic antibody, comprising reacting the agent with the catalytic antibody of claim 1, thereby conjugating the agent to the catalytic antibody.

13. The method of claim 12, wherein the agent is a drug moiety or a targeting moiety.

14. The method of claim 12, wherein the agent is a small molecule agent or a nucleic acid agent.

15. A pharmaceutical composition, comprising an effective amount of the antibody-agent conjugate of claim 6 and optionally a pharmaceutically acceptable carrier.

16. The antibody-agent conjugate of claim 9, wherein the tumor antigen is HER2.

17. A pharmaceutical composition, comprising an effective amount of the antibody-agent conjugate of claim 16 and optionally a pharmaceutically acceptable carrier.

18. A method for treating a HER2-positive cancer in a subject, comprising administering to the subject in need of treatment the pharmaceutical composition of claim 17.

* * * * *